(12) United States Patent
Geha

(10) Patent No.: US 11,707,221 B1
(45) Date of Patent: Jul. 25, 2023

(54) METHOD OF IDENTIFYING CHRONIC PAIN USING LOW FREQUENCY FLUCTUATIONS IN NUCLEUS ACCUMBENS

(71) Applicant: Paul Geha, Rochester, NY (US)

(72) Inventor: Paul Geha, Rochester, NY (US)

(73) Assignee: Paul Geha, Rochester, NY (US)

( * ) Notice: Subject to any disclaimer, the term of this patent is extended or adjusted under 35 U.S.C. 154(b) by 11 days.

(21) Appl. No.: 17/235,451

(22) Filed: Apr. 20, 2021

Related U.S. Application Data

(60) Provisional application No. 63/012,710, filed on Apr. 20, 2020.

(51) Int. Cl.
| | |
|---|---|
| *A61B 5/00* | (2006.01) |
| *G01R 33/56* | (2006.01) |
| *G16H 10/20* | (2018.01) |
| *G16H 50/70* | (2018.01) |
| *G01R 33/48* | (2006.01) |
| *A61B 5/16* | (2006.01) |

(52) U.S. Cl.
CPC ............ *A61B 5/4824* (2013.01); *A61B 5/165* (2013.01); *A61B 5/4064* (2013.01); *A61B 5/4848* (2013.01); *G01R 33/4806* (2013.01); *G01R 33/5608* (2013.01); *G16H 10/20* (2018.01); *G16H 50/70* (2018.01)

(58) Field of Classification Search
CPC ..... A61B 5/4824; A61B 5/165; A61B 5/4064; A61B 5/4848; G01R 33/4806; G01R 33/5608; G16H 10/20; G16H 50/70
See application file for complete search history.

(56) References Cited

U.S. PATENT DOCUMENTS

2005/0283053 A1\* 12/2005 deCharms .............. A61B 5/486
600/300

FOREIGN PATENT DOCUMENTS

WO WO-2014169060 A1 \* 10/2014 ............. A61B 5/055

OTHER PUBLICATIONS

Konno et al., Association Between Brain and Low Back Pain, Journal of Orthopaedic Science, 23 (2018) 3-7. (Year: 2018).\*
Seminowicz et al., Pain-Related Nucleus Accumbens Function: Modulation by Reward and Sleep Disruption, International Association for the Study of Pain, 160 (2019) 1196-1207. (Year: 2019).\*

\* cited by examiner

*Primary Examiner* — Susan S Lee
(74) *Attorney, Agent, or Firm* — DeLio Peterson & Curcio LLC; Brian G. Schlosser

(57) ABSTRACT

A method of identifying chronic pain in a patient including using functional magnetic resonance imaging (fMRI), performing a functional brain scan in the NAc (nucleus accumbens) of a patient brain including extracting activity from the NAc. Database information, which includes fMRI data obtained from healthy patients, may be compared to the extracted activity to determine if patient is a chronic pain patient. In patients with chronic pain, the method may be repeated to evaluate the effects of the treatment. A resting state brain scan may be performed initially, and a Fourier transform may be performed to obtain frequency content. The frequency bands of the method may be broken down to extract information in a 0.01-0.027 Hz frequency band.

18 Claims, 26 Drawing Sheets

|  | CLBP | SBP | HC | P-value |
|---|---|---|---|---|
| Age (years) | 32.2 ± 2.0 | 31.7 ± 1.7 | 31.1 ± 2.0 | 0.93 |
| Sample size (gender) | 28 (17 F) | 40 (16 F) | 30 (14 F) | 0.27 |
| Pain Duration | 5.5 ± 0.9 § | 9.4 ± 0.7 † | - | - |
| VAS | 4.7 ± 0.3 | 3.1 ± 0.3 | - | 0.005 |
| BDI | 6.9 ± 1.4 | 5.3 ± 0.7 | 2.4 ± 0.6 | 0.004 |
| BAI | 8.6 ± 2.3 | 6.7 ± 1.0 | 3.1 ± 1.0 | 0.038 |

*Abbreviations:* BDI, Beck's Depression Index; BAI, Beck's Anxiety Index; CLBP, Chronic Low Back Pain; SBP, Sub-Acute Back Pain; HC, Healthy Controls; VAS, Visual Analogue Scale. §, Duration in years; †, Duration in weeks.

Fig. 22

|  | Healthy | SBP | CLBP | P-value * |
|---|---|---|---|---|
| L NAc | 0.76 ± 0.02 | 0.69 ± 0.02 | 0.66 ± 0.02 | 0.0036 |
| R NAc | 0.62 ± 0.02 | 0.57 ± 0.02 | 0.57 ± 0.02 | 0.20 |
| L Amygdala | 1.57 ± 0.51 | 1.64 ± 0.44 | 1.71 ± 0.51 | 0.16 |
| R Amygdala | 1.57 ± 0.69 | 1.74 ± 0.60 | 1.67 ± 0.69 | 0.18 |
| L Hippocampus | 4.96 ± 0.10 | 4.99 ± 0.88 | 4.97 ± 0.99 | 0.98 |
| R Hippocampus | 5.16 ± 0.11 | 5.14 ± 0.96 | 5.09 ± 0.11 | 0.89 |
| L Thalamus | 10.7 ± 0.15 | 10.4 ± 0.13 | 10.4 ± 0.14 | 0.33 |
| R Thalamus | 10.4 ± 0.15 | 10.2 ± 0.13 | 10.1 ± 0.15 | 0.37 |
| *, P-values, from general linear model corrected for age and gender. | | | | |

Fig. 23

| Subjects | Baseline Scanned | Follow-up Tested | Follow-up Scanned |
|---|---|---|---|
| Age (years) | | | |
| SBPp | 34.3 ± 2.6 | 35.9 ± 2.5 | 39.0 ± 3.2 |
| SBPr | 31.0 ± 2.4 | 32.1 ± 2.3 | 33.4 ± 2.7 |
| HC | 30.3 ± 2.6 | 31.6 ± 2.5 | 32.6 ± 2.8 |
| *Group effects* | 0.51 | 0.51 | 0.28 |
| Sample Size (Gender) | | | |
| SBPp | 16 (6 F) | 16 (6 F) | 11 (5F) |
| SBPr | 19 (8 F) | 19 (8 F) | 15 (8F) |
| HC | 30 (14 F) | 16 (7 F) | 14 (7F) |
| *Group effects* | 0.83 | 0.93 | 0.92 |
| Pain Duration (weeks) | | | |
| SBPp | 9.9 ± 0.9 | 93.1 ± 7.4 | 91.4 ± 8.2 |
| SBPr | 9.1 ± 0.9 | 68.7 ± 6.8 | 65.7 ± 7.0 |
| HC | - | - | - |
| *Group effects* | 0.55 | < 0.05 | < 0.05 |
| Weeks at follow-up | | | |
| SBPp | - | 83.2 ± 9.8 | 80.6 ± 7.9 |
| SBPr | - | 59.2 ± 4.3 | 55.9 ± 6.8 |
| HC | - | 68.8 ± 5.4 | 68.6 ± 7.0 |
| | | 0.07 | 0.07 |
| Pain Intensity | | | |
| SBPp | 3.0 ± 0.4 | 3.7 ± 0.3 | 3.8 ± 0.4 |
| SBPr | 3.5 ± 0.4 | 1.2 ± 0.3 | 1.4 ± 0.4 |
| HC | - | | - |
| *Group effects* | 0.36 | $< 10^{-5}$ | $< 10^{-4}$ |
| PCS | | | |
| SBPp | 8.8 ± 2.3 | 9.0 ± 1.4 | 9.0 ± 1.8 |
| SBPr | 12.6 ± 2.1 | 6.4 ± 1.3 | 6.8 ± 1.5 |
| HC | - | - | - |
| *Group effects* | 0.24 | 0.19 | 0.35 |
| BDI | | | |
| SBPp | 3.0 ± 1.0 | 4.6 ± 1.4 | 4.3 ± 1.6 |
| SBPr | 7.3 ± 0.9 | 4.4 ± 1.3 | 4.5 ± 1.4 |
| HC | 2.2 ± 1.0 | 2.4 ± 1.3 | 2.7 ± 1.5 |
| *Group effects* | $< 10^{-3}$ | 0.44 | 0.64 |
| BAI | | | |
| SBPp | 4.8 ± 1.6 | 4.7 ± 1.5 | 4.6 ± 1.9 |
| SBPr | 8.0 ± 1.4 | 5.5 ± 1.4 | 5.5 ± 1.7 |
| HC | 2.3 ± 1.5 | 3.8 ± 1.5 | 4.4 ± 1.7 |
| *Group effects* | < 0.05 | 0.71 | 0.88 |
| NPS | | | |
| SBPp | 20.9 ± 3.0 | 20.5 ± 3.3 | 22.4 ± 4.1 |
| SBPr | 21.7 ± 2.7 | 10.7 ± 3.1 | 10.7 ± 3.5 |
| HC | - | - | |
| *Group effects* | 0.84 | < 0.05 | < 0.05 |
| MPQt | | | |
| SBPp | 8.0 ± 1.2 | 7.8 ± 1.2 | 8.3 ± 1.5 |
| SBPr | 9.0 ± 1.1 | 4.7 ± 1.1 | 4.5 ± 1.2 |
| TAHC | - | - | |
| *Group effects* | 0.54 | 0.06 | 0.06 |

*Abbreviations*: BDI, Beck's Depression Index; BAI, Beck's Anxiety Index; MPQ, short form of the McGill Pain Questionnaire; PCS, Pain Catastrophizing Scale; NPS, Neuropathic Pain Scale.

Fig. 24

| Subjects | Baseline | Follow-up | Time Effects |
|---|---|---|---|
| | L NAc | | |
| SBPp | 0.66 ± 0.03 | 0.68 ± 0.04 | |
| SBPr | 0.72 ± 0.02 | 0.70 ± 0.03 | p = 0.40 |
| HC | 0.76 ± 0.02 | 0.79 ± 0.03 | |
| *Group effects* | p < 0.05 | p < 0.05 | |
| | R NAc | | |
| SBPp | 0.58 ± 0.03 | 0.53 ± 0.04 | |
| SBPr | 0.57 ± 0.03 | 0.59 ± 0.03 | p = 0.33 |
| HC | 0.62 ± 0.02 | 0.59 ± 0.03 | |
| *Group effects* | p = 0.39 | p = 0.52 | |
| | L Amygdala | | |
| SBPp | 1.56 ± 0.69 | 1.66 ± 0.10 | |
| SBPr | 1.70 ± 0.61 | 1.74 ± 0.09 | p = 0.95 |
| HC | 1.57 ± 0.49 | 1.54 ± 0.08 | |
| *Group effects* | p = 0.19 | p = 0.27 | |
| | R Amygdala | | |
| SBPp | 1.64 ± 0.98 | 1.74 ± 0.12 | |
| SBPr | 1.79 ± 0.87 | 1.70 ± 0.10 | p = 0.84 |
| HC | 1.57 ± 0.70 | 1.61 ± 0.10 | |
| *Group effects* | p = 0.16 | p = 0.61 | |
| | L Hippocampus | | |
| SBPp | 4.88 ± 0.14 | 4.97 ± 0.16 | |
| SBPr | 5.10 ± 0.12 | 5.22 ± 0.14 | p = 0.19 |
| HC | 4.96 ± 0.10 | 5.17 ± 0.14 | |
| *Group effects* | p = 0.48 | p = 0.74 | |
| | R Hippocampus | | |
| SBPp | 5.00 ± 0.16 | 5.04 ± 0.17 | |
| SBPr | 5.27 ± 0.14 | 5.17 ± 0.14 | p = 0.053 |
| HC | 5.16 ± 0.12 | 5.17 ± 0.14 | |
| *Group effects* | p = 0.45 | p = 0.74 | |
| | L Thalamus | | |
| SBPp | 10.22 ± 0.19 | 10.52 ± 0.20 | |
| SBPr | 10.59 ± 0.17 | 10.81 ± 0.16 | p = 0.39 |
| HC | 10.67 ± 0.14 | 10.85 ± 0.16 | |
| *Group effects* | p = 0.15 | p = 0.32 | |
| | R Thalamus | | |
| SBPp | 10.13 ± 0.19 | 10.40 ± 0.21 | |
| SBPr | 10.32 ± 0.17 | 10.53 ± 0.17 | p = 0.69 |
| HC | 10.42 ± 0.14 | 10.64 ± 0.17 | |
| *Group effects* | p = 0.49 | p = 0.74 | |

Fig. 25

|  | Baseline Pain (VAS) | Change in Pain | LNAc volume | RNAc volume |
|---|---|---|---|---|
| Age | 0.20 | -0.17 | 0.00 | -0.06 |
| BDI | -0.08 | 0.04 | 0.04 | -0.14 |
| BAI | 0.19 | 0.17 | -0.02 | -0.22 |
| Duration | -0.01 | -0.17 | 0.05 | 0.19 |
| Baseline Pain (VAS) | 0.00 | 0.58 | -0.03 | 0.07 |

Fig. 26

|  | SBPr | SBPp | p-value |
|---|---|---|---|
| Age (years) | 43.8 ± 3.1 | 46.6 ± 2.2 | 0.47 |
| Sample size (gender) | 10 (6 F) | 20 (9 F) | 0.44 |
|  | CLBP | HC |  |
| Age (years) | 46.9 ±1.9 | 37.5 ± 1.6 | $< 10^{-3}$ |
| Sample size (gender) | 14 (6 F) | 19 (8 F) | 0.95 |

Fig. 27

METHOD OF IDENTIFYING CHRONIC PAIN USING LOW FREQUENCY FLUCTUATIONS IN NUCLEUS ACCUMBENS

This application claims priority to U.S. Provisional Patent Application Ser. No. 63/012,710 filed on Apr. 23, 2020, the entire disclosure of which is incorporated herein by reference.

BACKGROUND OF THE INVENTION

1. Field of the Invention

The present invention relates to measuring brain biomarkers to detect chronic pain using functional magnetic resonance imaging and, more specifically, measuring brain biomarkers using specific frequency bands within the nucleus accumbens of the brain.

2. Description of Related Art

Chronic pain is a highly prevalent disease with poorly understood pathophysiology. In particular, the brain mechanisms mediating the transition from acute to chronic pain remain largely unknown. Sub-acute back pain patients who are at risk of developing chronic pain exhibit a smaller nucleus accumbens volume, which persists in the chronic phase, compared to healthy controls. The smaller accumbens volume was also observed in a separate cohort of chronic low back pain patients and was associated with dynamic changes in functional connectivity. At baseline sub-acute back pain patients showed altered local nucleus accumbens connectivity between putative shell and core irrespective of the risk of transition to chronic pain.

Two recent fMRI studies suggest that the risk of transitioning from acute to chronic pain may be determined by the physiology of the limbic brain. In addition, pre-clinical studies have provided evidence that the limbic brain plays a causal role in the modulation of peripheral nociception and in the transition to chronic pain. However, a state-specific biomarker for chronic pain is still unknown and a robust reproducible biomarker remains undefined.

The prevalence of chronic pain has reached epidemic levels. In addition to personal suffering chronic pain is associated with psychiatric and medical co-morbidities, notably substance misuse. Chronic pain currently does not have a cure or quantitative diagnostic or prognostic tools.

SUMMARY OF THE INVENTION

At follow-up, connectivity changes were observed between nucleus accumbens and rostral anterior cingulate cortex in the patients with persistent pain. Analysis of the power spectral density of nucleus accumbens resting state activity in the sub-acute and chronic back pain patients revealed loss of power in the slow-5 frequency band (0.01-0.027 Hz) which developed only in the chronic phase of pain. This loss of power was reproducible across two cohorts of chronic low-back pain patients obtained from different sites, and accurately classified chronic low-back pain patients in two additional independent data sets. The results provide evidence that lower nucleus accumbens volume confers risk for developing chronic pain and altered nucleus accumbens activity is a signature of the state of chronic pain.

It was shown that brain imaging can provide such measures. First, it was shown that the brain limbic system of patients with sub-acute back pain at risk of becoming chronic back pain patients exhibit limbic system structural alterations which predates the onset of chronic pain. Second, it was shown that the nucleus accumbens activity shows loss of low frequency fluctuations only when patients transition to the chronic phase an observation that was reproduced in multiple data sets collected at different sites.

Functional MRI Explanation

In a brain the activity of the neurons constantly fluctuates as you engage in different activities, from simple tasks like controlling a hand to reach out and pick up a cup of coffee to complex cognitive activities like understanding language in a conversation. The brain also has many specialized parts, so that activities involving vision, hearing, touch, language, memory, etc. have different patterns of activity. Even when you rest quietly with eyes closed the brain is still highly active, and the patterns of activity in this resting state are thought to reveal particular networks of areas that often act together. Functional magnetic resonance imaging (fMRI) is a technique for measuring and mapping brain activity that is noninvasive and safe. It is being used in many studies to better understand how the healthy brain works, and in a growing number of studies it is being applied to understand how that normal function is disrupted in disease. When neural activity increases in a particular area of the brain, the MR signal also increases by a small amount. Although this effect involves a signal change of only about 1%, it is still the basis for most of the fMRI studies done today.

Bearing in mind the problems and deficiencies of the prior art, it is therefore an object of the present invention to provide a method for using brain imaging to detect chronic pain in a patient or subject.

It is another object of the present invention to provide a method of detecting chronic pain by determining nucleus accumbens activity shows loss of low frequency fluctuations when patients transition to the chronic phase of pain.

A further object of the invention is to provide a method of determining the state of chronic pain using analysis of the power spectral density (PSD) of nucleus accumbens resting state activity where there is a loss of power in the 0.01-0.027 Hz frequency band.

It is yet another object of the present invention to provide a method for using a state-specific biomarker for verifying chronic pain.

Still other objects and advantages of the invention will in part be obvious and will in part be apparent from the specification.

The above and other objects, which will be apparent to those skilled in the art, are achieved in the present invention which is directed to a method of identifying chronic pain in a patient comprising using fMRI, performing a functional brain scan in the NAc of a patient brain including extracting activity from the NAc. The method includes using the extracted activity to compare to database information, the database information including fMRI data obtained from healthy subjects and using the compared data to determine if patient is a chronic pain patient. The method may include initially performing a resting state brain scan. The method may include after the step of using the compared data to determine if patient is a chronic pain patient, treating the patient and repeating the steps to evaluate the effect of the treatments. The method may include an initial step of confirming patient experiencing pain of at least 20/100 on a visual analogue scale. The step of using the extracted activity to compare to database information may include calculating a normalization coefficient. The method may include an initial step of distributing questionnaire to patient, the questionnaire including pain level and mood and anxiety levels. The resting state brain scan may use BOLD as a measure. The method may include after the step of extracting activity from NAc, performing a Fourier transform to obtain frequency content. The method may include breaking down the frequency bands to extract information in a 0.01-0.027 Hz frequency band during the step of performing a functional brain scan in the NAc of a patient brain. The method may include using the extracted activity to compare to database information obtained from scans of a plurality of healthy individuals. The data information may include measured activity obtained from scans of a plurality of healthy individuals. The database information may include cutoff measurements for determining if the patient is a chronic pain patient.

Another aspect of the present invention is directed to a method of identifying chronic pain using low frequency fluctuations in nucleus accumbens comprising performing a functional brain scan extracting activity from NAc and performing a Fourier transform to obtain content within a 0.01-0.027 Hz frequency band. The method includes using the extracted activity to compare to database information which includes cutoff measurements for determining if the patient is a chronic pain patient and using the compared data to determine if patient is a chronic pain patient. The method may include after the step of using the compared data to determine if patient is a chronic pain patient, treating the patient and repeating the first 3 to evaluate the effect of the treatments.

Another aspect of the present invention is directed a method of identifying chronic pain in a patient comprising using fMRI to monitor activity of a plurality of healthy subjects in the NAc of each subject's brain within a 0.01-0.027 Hz frequency band and enter measured data from the monitored activity into a database. The method includes determining distribution of the measured data in the healthy subjects to determine cutoff on measure for healthy patient, performing a functional scan of the patient, comparing to healthy subject data in the database and determining if the patient is a chronic pain patient. The method may include performing a Fourier transform analysis and using the slow5 frequency to determine if the patient is a chronic pain patient.

Another aspect of the present invention is directed to a method of identifying chronic pain in a patient comprising using fMRI, monitor activity of a plurality of healthy subjects in the nucleus accumbens of each subject's brain within a 0.01-0.027 Hz frequency band and enter measured data from the monitored activity into a database. The method includes determining distribution of the measured data in the healthy subjects to determine cutoff on measure for healthy patient, performing a resting state scan of the nucleus accumbens using BOLD as a measure and extracting activity from nucleus accumbens. The method includes performing a Fourier transform to obtain content within a 0.01-0.027 Hz frequency band, using the extracted activity to compare to database information which includes cutoff measurements for determining if the patient is a chronic pain patient and using the compared data to determine if patient is a chronic pain patient. The method may include extracting activity from the nucleus accumbens includes analysis of the power spectral density of nucleus accumbens resting state activity where there is a loss of power in the 0.01-0.027 Hz frequency band. The method may include performing a Fourier transform analysis at the 0.01-0.027 Hz frequency band to determine if the patient is in a state of chronic pain. The method may include after the step of using the compared data to determine if patient is a chronic pain patient, treating the patient and repeating the steps of performing a resting state scan of the nucleus accumbens using BOLD as a measure, extracting activity from nucleus accumbens, performing a Fourier transform to obtain content within a 0.01-0.027 Hz frequency band and using the extracted activity to compare to database information which includes cutoff measurements for determining if the patient is in a state of chronic pain.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 22 is a tabular view showing demographic and clinical characteristics of all participants at baseline.

FIG. 23 is a tabular view showing group averaged sub-cortical volumes in centimeter cube (cc) units for healthy, SBP and CLBP subjects.

FIG. 24 is a tabular view showing demographics and clinical characteristics of all SBPp, and SBPr patients and healthy controls (HC) at baseline and at follow-up. Since not all SBP patients underwent both testing and scanning at follow-up this time-point has two different entries.

FIG. 25 is a tabular view showing sub-cortical volumes in cc at baseline and at follow-up in SBPp, SBPr patients and in HC. P-values obtained from GLM analysis with group and time as factors, corrected for age and gender.

FIG. 26 is a tabular view showing that the correlation analysis reveals no significant relationship between left or right NAc volumes and demographic patients' characteristics, or mood and anxiety ratings. Only baseline pain correlated significantly with change in pain at follow-up (r=0.58; p<0.01). Change in pain was calculated as VAS ratings at follow-up minus VAS ratings of back pain at baseline.

FIG. 27 is a tabular view showing demographic data for patients and healthy controls used to test the predictive model.

DESCRIPTION OF THE EMBODIMENT(S)

In describing the preferred embodiment of the present invention, reference will be made herein to FIGS. 1-27 of the drawings in which like numerals refer to like features of the invention.

Chronic pain is a huge burden to individuals and society. It decreases quality of life leading sometimes to disability, predisposes patients to other co-morbidities such as substance misuse and causes billions of dollars in economic losses every year. The pathophysiology of chronic pain in humans has been subject to intensive investigation with functional brain imaging in the past two decades in the hope of identifying brain circuits that underlie the risk and the subjective experience of chronic pain. This endeavor is critical to uncovering biomarkers of this condition that could inform diagnosis, prevention and novel treatments.

In the present study the structural and functional properties of limbic structures (amygdala, accumbens, hippocampus and thalamus) in healthy participants examined, and in patients suffering from sub-acute back pain (SBP) and in patients suffering from CLBP. After initial testing, we also followed the SBP patients and healthy participants longitudinally after the initial testing and identified patients who persist in having pain (SBPp) and patients who recover (SBPr). Specifically, sub-cortical brain volumes and resting state brain activity was measured. These analyses revealed two novel findings about the role of the brain in risk and development of chronic pain. First, a smaller nucleus accumbens volume predates the development of chronic pain and remains unchanged at follow-up, suggesting that it plays a role in risk for development of chronic pain. Second, alterations in low-frequency (0.01-027 Hz) oscillations at rest in the nucleus accumbens develops only after the onset of the chronic pain phase, suggesting that it is a signature of the state of chronic pain.

Results

The volume of the nucleus accumbens is smaller in sub-acute and chronic low-back pain patients.

Figure 7:
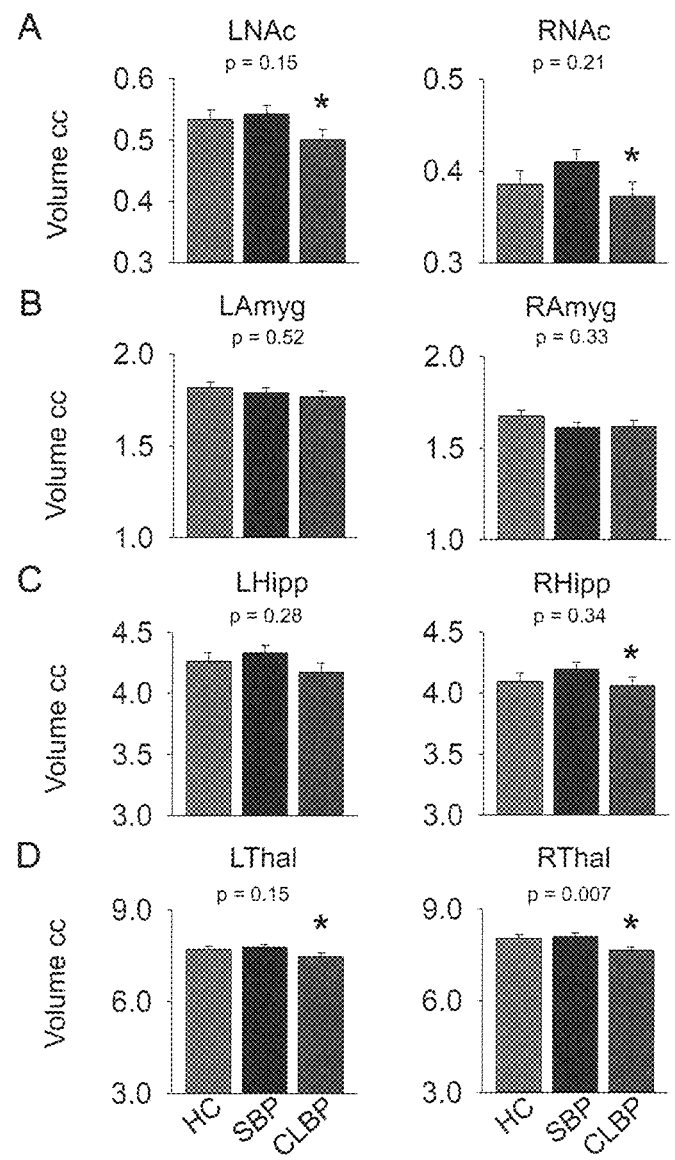
FIG. 7 shows sub-cortical volumes in sub-acute and chronic low back pain extracted with Freesurfer. (A) There was no significant difference comparing LNAc $(F(2.92)=1.92, p=0.15)$ and RNAc $(F(2.92)=1.61, p=0.20)$ volumes of SBP and CLBP patients to healthy controls, but post-hoc analysis showed significantly decreased volume of left and right NAc in CLBP patients ($p<0.05$). (C-D) No significant differences between SBP, CLBP and healthy controls were observed in amygdala, hippocampus, and thalamus, except for right thalamus (F $(2,92)=5.27, p=0.007$). *, $p<0.05$ for the post-hoc analysis.
Figure 8:
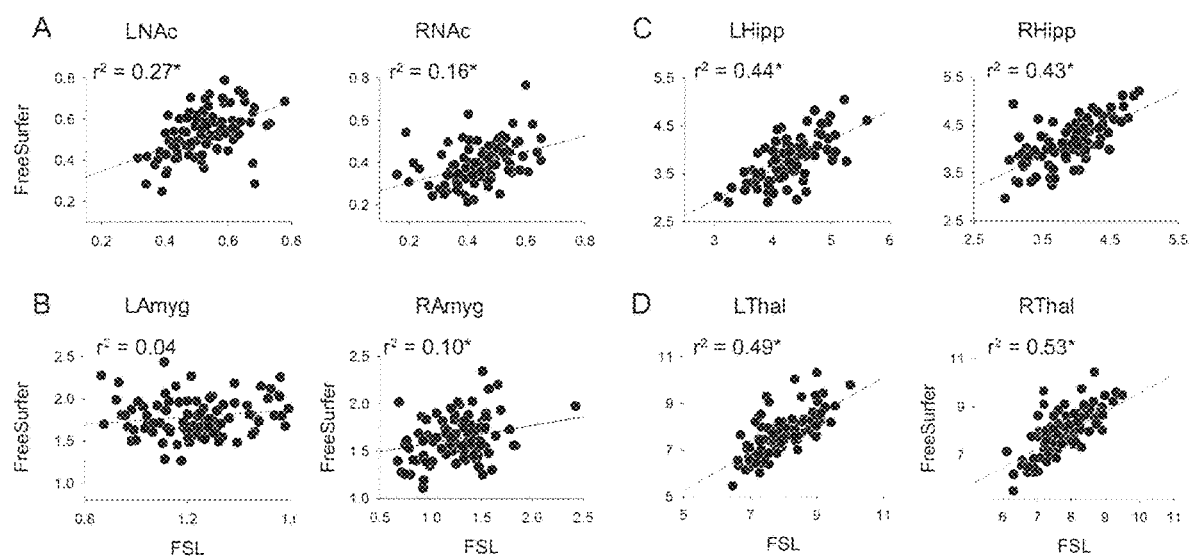
FIG. 8 shows comparisons of sub-cortical volumes extracted with FIRST to those extracted with Freesurfer. Correlations of the measures of sub-cortical volumes between FIRST and Freesurfer are weaker for small structures (NAc and amygdala) (A-B) and stronger for large structures (hippocampus and thalamus) (C-D). Values shown are uncorrected for intracranial volume *, $p<0.05$.
Figure 9:
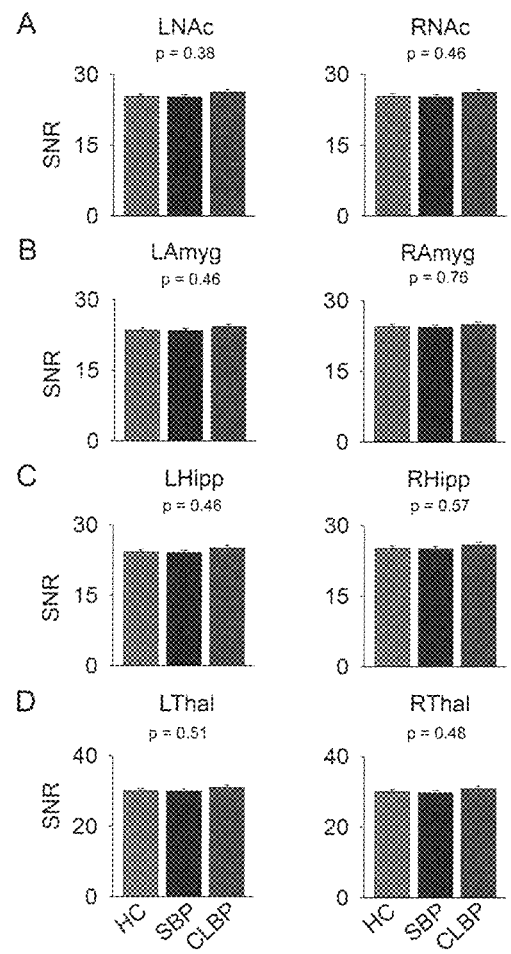
FIG. 9 shows signal to noise ratio (SNR) calculated as mean signal within the sub-cortical structure mask divided by the standard deviation outside the brain. There was no significant difference in SNR between the groups. P-value, one-way ANOVA.

The left nucleus accumbens (LNAc) showed a significant decrease in volume when healthy participants, were compared to SBP and CLBP patients ($F_{(2,93)}=6.0$; $p=0.004$; Cohen's $d=0.70$) (healthy volume=$0.76\pm0.02$; SBP volume=$0.69\pm0.02$; CLBP=$0.66\pm0.02$ cc) (FIGS. 1A and 23). Post-hoc Tukey honestly significant difference (HSD) showed that the LNAc was significantly smaller in SBP ($p=0.034$) and CLBP patients ($p=0.003$) compared to healthy participants. There was no group effect in the right NAc (RNAc) ($p=0.20$). No difference in the hippocampus or amygdala volumes between healthy participants and back pain patients (FIG. 6) was found. The volumetric analysis using FreeSurfer was repeated. The GLM analysis for LNAc ($p=0.15$) and RNAc ($p=0.21$) were not significant but post-hoc HSD showed that CLBP patients show significantly smaller LNAc ($p=0.02$) and RNAc ($p=0.036$) than SBP patients (FIG. 7). The correlations between the volumetric values obtained with FIRST and those obtained with Free-Surfer was examined. The two protocols give weakly correlated results in smaller structures (i.e. NAc and amygdala) and strongly correlated results in larger structures (i.e. hippocampus and thalamus) (FIG. 8), similar to a previous report. This explains to a large part the discrepancy observed in the NAc volume obtained from the two sub-cortical extraction protocols. Signal to noise ratio (SNR) was not different for any sub-cortical structure when comparing healthy controls, SBP and CLBP participants (FIG. 9).

NAc volume is smaller in SBP patients with persistent pain at follow-up.

Figure 1:
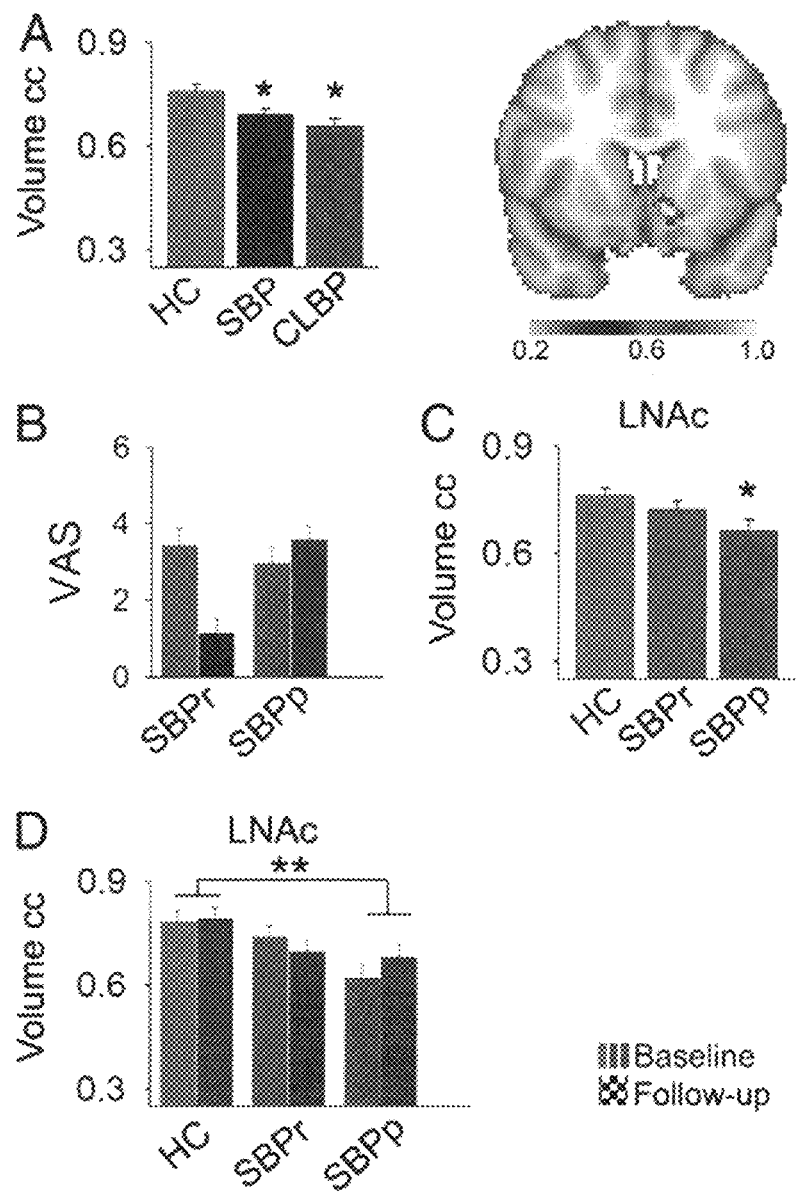
FIG. 1 shows a chart comparing NAc volumes in sub-acute and chronic low-back pain patients.
Figure 5:
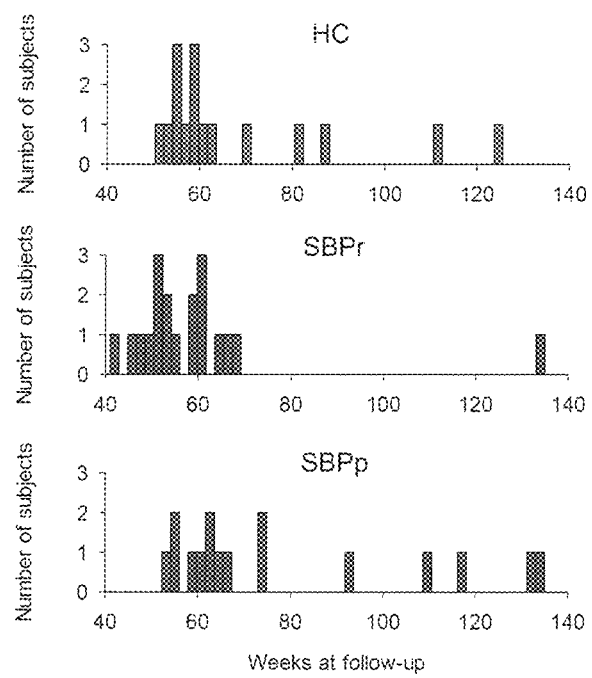
FIG. 5 shows Histogram plots showing the distribution of the number of weeks at follow-up for HC (green), SBPr (blue) and SBPp (red). The median duration at follow-up was 59.5 weeks.
Figure 6:
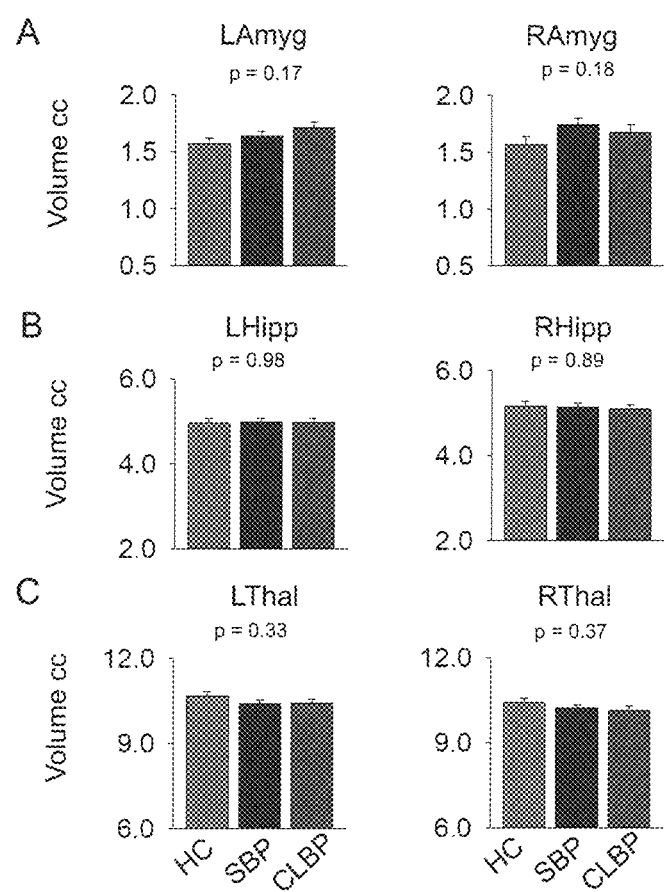
FIG. 6 is a chart showing sub-cortical volumes in sub-acute and chronic low back pain extracted using FIRST from FSL. There were no significant differences between SBP or CLBP patients and healthy controls in amygdala, hippocampus or thalamus volumes (A-C). Abbreviations, Amyg, amygdala; Hipp, hippocampus; Thal, thalamus. P-values from general linear model corrected for age and sex.
Figure 10:
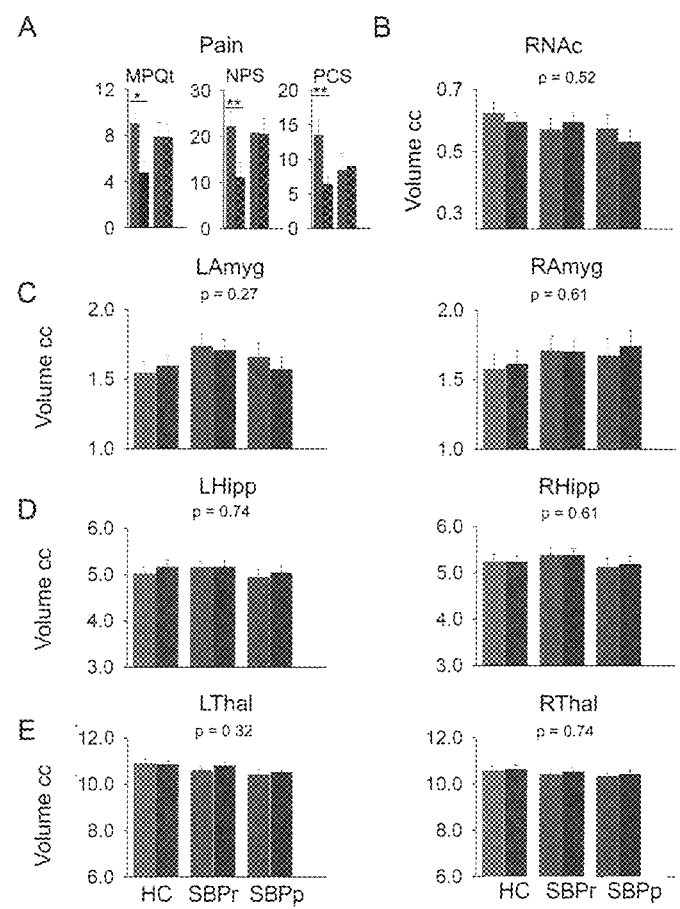
FIG. 10 shows a comparison of sub-cortical volumes extracted using FIRST between SBPp, SBPr, and healthy controls at entry into the study at follow-up. (A) Bar plot showing reported low back pain intensity in MPQ, NPS and PCS scores in SBPp and SBPr patients at entry into the study and at follow-up. SBPr patients improved significantly on all 3 measures but SBPp patients' pain experience did not change. (B-E) Sub-cortical volumes in SBPp and SBPr patients compared to healthy controls at entry into the study and at follow-up. *, p<0.05; **, p<0.01.
Figure 11:
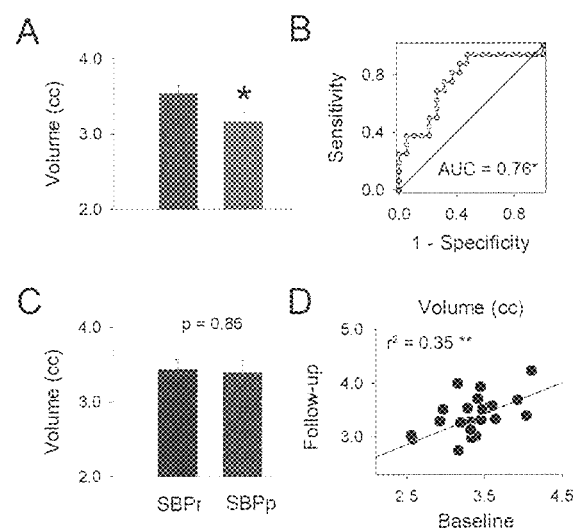
FIG. 11 shows that Amygdala volume is different at baseline between SBPr and SBPp patients and accurately predicts long-term outcome. (A) SBPr patients show a significantly larger amygdala volume (left+right) at baseline (p<0.05, corrected for age and sex). (B) Receiver operating characteristic curve shows accurate classification of SBPr and SBPp patients using baseline amygdala volumes (AUC=area under the curve, p<0.05). (C) SBPr and SBPp patients are no longer significantly different in their amygdala volume at follow-up. This result is consistent with the CLBP data where a trend towards increased amygdala volume in CLBP patients (FIG. 6) was observed. (D) Scatterplot of the correlation between baseline and follow-up amygdala volumes. **, p<0.01
Figure 12:
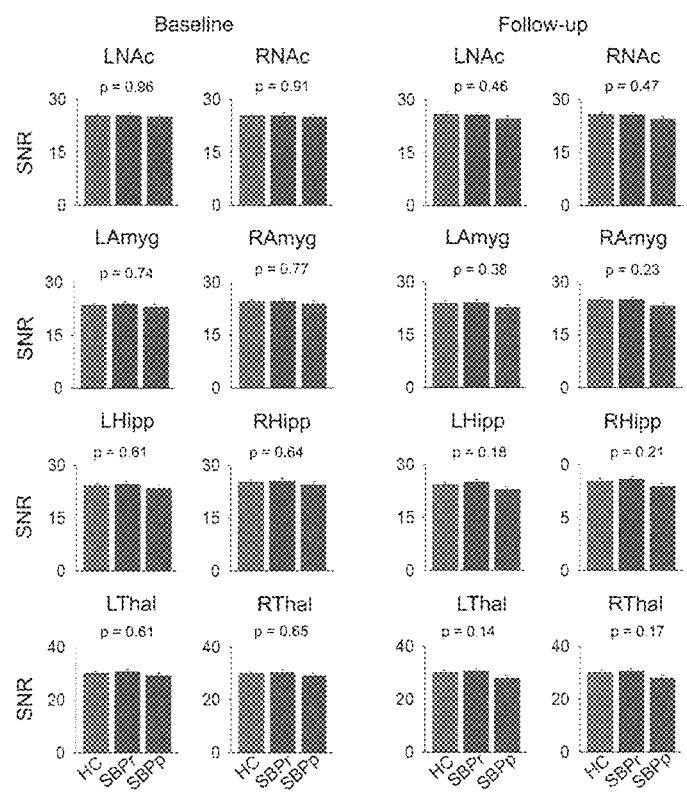
FIG. 12 shows SNR was not different between HC, SBPr and SBPp at baseline or at follow-up. There was no significant effect of time or significant time x group interaction. P-value, group effects one-way ANOVA.
Figure 13:
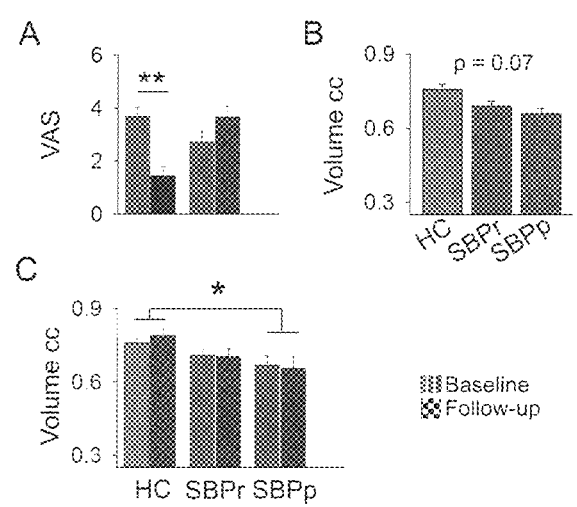
FIG. 13 shows the comparison of left NAc volumes when criterion for recovery from back pain is defined as a 20% reduction in pain intensity from baseline. (A) Back pain intensity ratings in SBPr (light blue) and SBPp (red) patients at baseline and at follow-up. (B) The LNAc volume is decreased in SBPp patients at baseline compared to healthy control (F(2.58)=2.78, p=0.07; post-hoc comparison to HC, p=0.055, 13 SBPp, 22 SBPr and 30 HC). (C) The significant difference between the groups is apparent when a group x time analysis is performed (F(2.33)=4.87, p=0.014; 9 SBPp, 17 SBPr and 14 HC).
Figure 14:
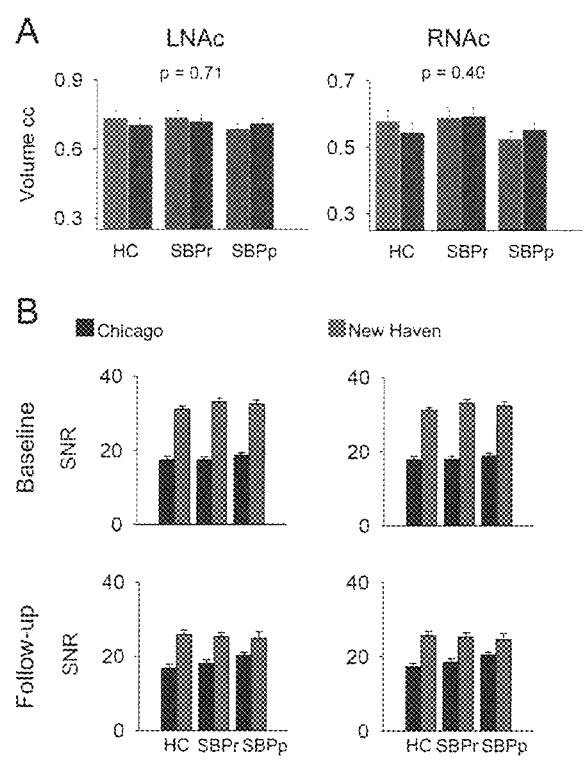
FIG. 14 shows the nucleus accumbens volume in data available from openpain.org showing a significant decrease in SBPp patients at baseline only. (A) Left and right NAc volume at baseline (plain color) and at follow-up (checkered color). The p-values shown are calculated from repeated measures analysis. However, examining the volumes at baseline only shows a group effect at p=0.1 with post-hoc analysis showing a significant decrease in LNAc volume in SBPp patients compared to HC (p=0.028). The same analysis applied to the right NAc shows a group effect at p=0.12 with post-hoc analysis showing p=0.06 for the RNAc volume comparison between SBPp and HC. (B) Comparison of SNR between the data collected in New Haven and the data from openpain.org for left and right NAc, at baseline and one-year follow-up. All comparisons show a site effect with a $p<10^{-6}$).

Thirty-five SBP patients and 16 healthy controls were followed after a median of 59.5 weeks; 19 patients reported ≥30% improvement in their back-pain intensity and were considered recovered (SBPr) and 16 patients reported persistent back pain (SBPp) (FIG. 1B). Average duration of follow-up varied between groups because of outliers (FIG. 5). Some participants were only available after more than 2 years of the initial baseline visit. (FIGS. 5 and 24). At entry into the study SBPp and SBPr patients did not differ on reported back pain intensity (SBPp, $3.0\pm0.4$; SBPr=$3.5\pm0.4$, $p=0.36$, unpaired t-test) or the duration of back pain (SBPp, $9.9\pm0.9$; SBPr, $9.1\pm0.9$ weeks, $p=0.55$) (FIG. 24); however, SBPr patients showed significantly higher BDI ($p<10^{-3}$, ANOVA) and BAI ($p<0.05$) scores than SBPp and healthy controls at baseline. Nevertheless, the BDI and BAI scores of SBPr patients fell within the mild depressive and mild anxiety range (FIG. 24). SBPr patients showed significant improvement in their pain scores at follow-up measured using VAS, the short form of MPQ, the NPS and the PCS, and significant improvement in their mood but not their anxiety scores, while SBPp patients ratings did not show any change at follow-up (FIGS. 10A and 24). To investigate whether the decreased LNAc volume is present in SBPp patients at risk of transitioning to CLBP, sub-cortical volumes of healthy controls (n=30), SBPp (n=16) were compared to SBPr (n=19) patients. At baseline, the volume of LNAc in SBPp patients was significantly smaller than the LNAc volume of healthy controls (and comparable to that in CLBP patients) ($F_{(2,59)}=3.69$; $p<0.05$; Cohen's $d=0.70$) (FIG. 1C). Post-hoc comparison showed that SBPp patients had significantly ($p=0.017$) smaller LNAc volume compared to healthy controls. A sub-set (26 SBP patients and 14 HC) of these participants underwent also another fMRI scanning session at follow-up. Examining the volume of LNAc at follow-up showed persistence in the pattern observed at baseline where SBPp patients (n=11) showed a significantly smaller LNAc compared to healthy controls (n=14) and SBPr (n=15) (GLM with repeated measures, $F_{(2,34)}=5.1$; $p=0.012$; Cohen's $d=1.1$) (FIGS. 1D and 25). There was no change in the volume of LNAc between the two time points ($p=0.40$). Since duration at follow-up varied between groups, the GLM analysis was repeated after adding duration at follow-up as a variable of no interest. The results remained unchanged with groups showing significant difference ($F_{(2,33)}=4.8$; $p=0.015$). This is expected given that LNAc volume does not significantly change in time. No differences in the RNAc between SBPp, SBPr and HC subjects were observed (FIG. 10B). NAc volume was not correlated to demographic parameters or measures of pain, anxiety or depression (FIG. 26). No significant differences in the volumes of amygdala or hippocampus in SBPp patients compared to SBPr patients or healthy controls at any visit of the study while using a repeated measures group x time analysis (FIGS. 10 and 25) was observed. However, examining baseline and follow-up volumes separately shows that SBPp patients have a significantly smaller amygdala volume than SBPr patients (adding left and right) at baseline as reported previously, but not at follow-up (FIG. 11). Signal to noise ratio (SNR) was not different for any sub-cortical structure when comparing healthy controls, SBPr and SBPp participants (FIG. 12). The longitudinal results suggest that the volume of NAc is altered in SBPp patients by 6-16 weeks after the onset of back pain and remains unchanged at long-term follow-up. Since previous reports used 20% drop in back pain intensity at follow-up as a criterion defining recovery, the volumetric analysis was repeated after defining SBPr patients as such if their pain drops by 20%. As a result, 3 SBP patients whose reduction in pain intensity fell between 20-30% were now considered recovered. FIG. 13 shows that the volumetric results in the LNAc are almost identical. Next it was asked whether decreased LNAc volume in SBPp patients is reproducible across different sites in patients made accessible through http//:www.openpain.org. Therefore, using an identical analysis to the one applied to the data in FIG. 1, we compared sub-cortical volumes from SBPp (n=32; 26 at one year follow-up) and SBPr (n=22; 17 at one year follow-up)) patients and HC (n=18;17 at one year follow-up) groups using a within subject repeated measures ANCOVA that accounts for age, sex and intracranial volume. While a significantly smaller LNAc volume (p=0.03, post-hoc comparison to HC) was found and a trend (p=0.06) towards significance in the right NAc volume of SBPp patients at baseline, no significant volumetric difference between the groups at follow-up (FIG. 14A) was observed. However, when studying SNR it was observed that the data available online has a significantly smaller SNR than the data at all time points ($p<10^{-6}$) (FIG. 14B). The lower SNR can explain, at least in part, the discrepancy between sites given the NAc's small size.

SBPp and SBPr show differences in cortico-striatal functional connectivity of putative NAc shell and core.

Figure 2:
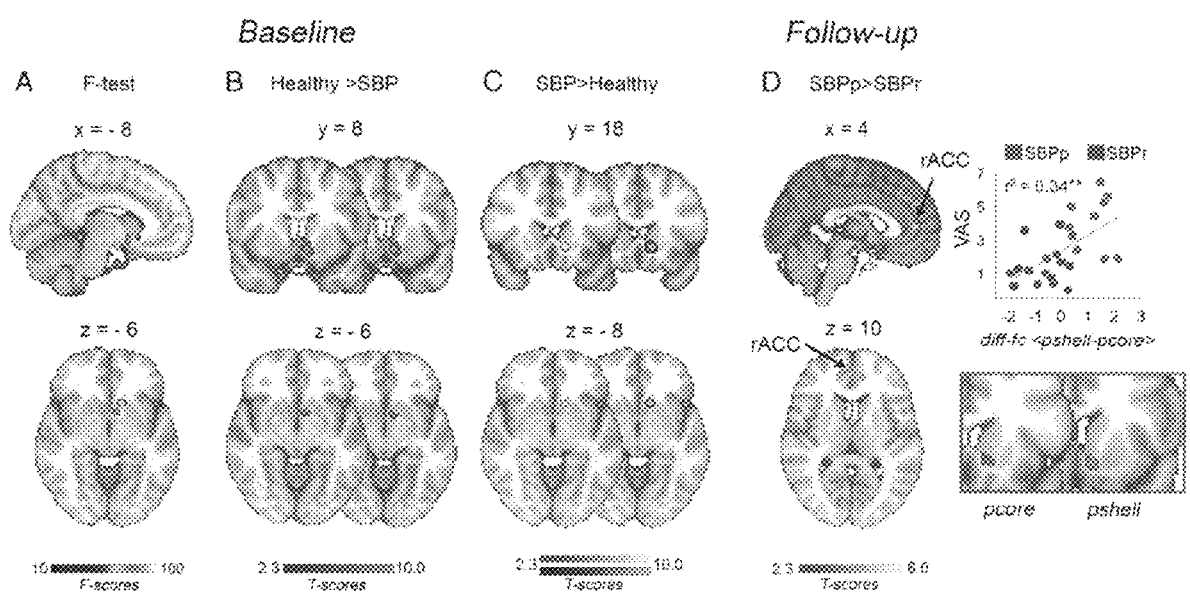
FIG. 2 shows the functional connectivity of the NAc.
Figure 3:
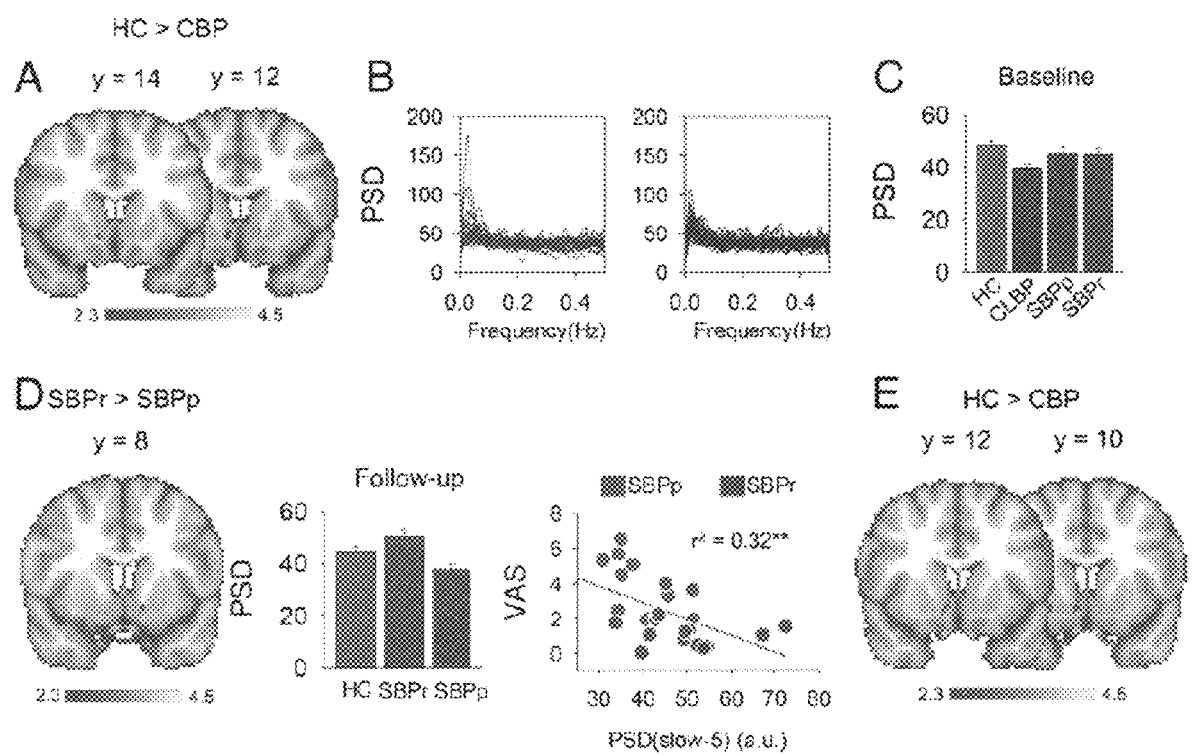
FIG. 3 shows power losses in the NAc within the slow-5 frequency band.
Figure 4:
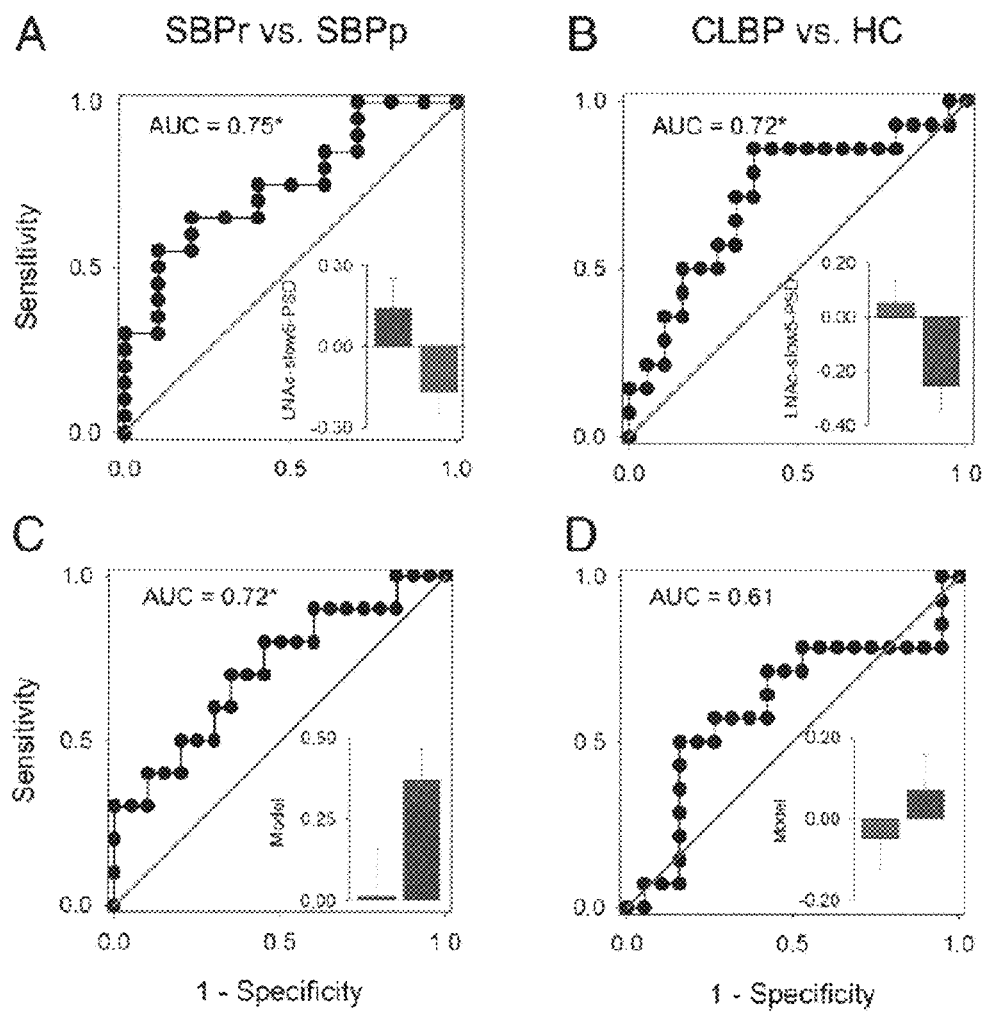
FIG. 4 is a histogram plot showing the average slow-5 PSD in LNAc within dataset groups.
Figure 15:
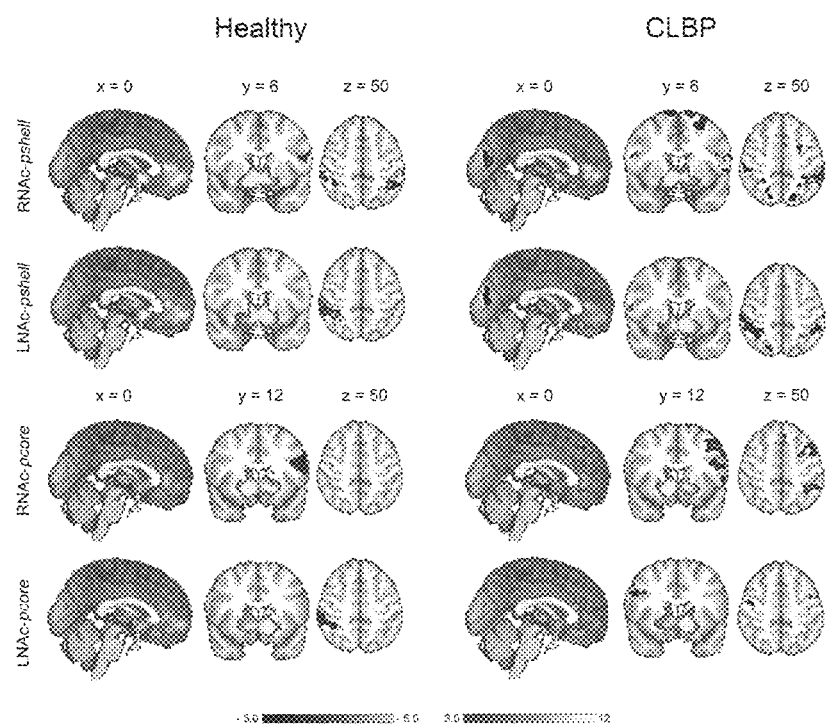
FIG. 15 shows average seed connectivity maps for putative NAc shell and core in healthy and CLBP patients.
Figure 16:
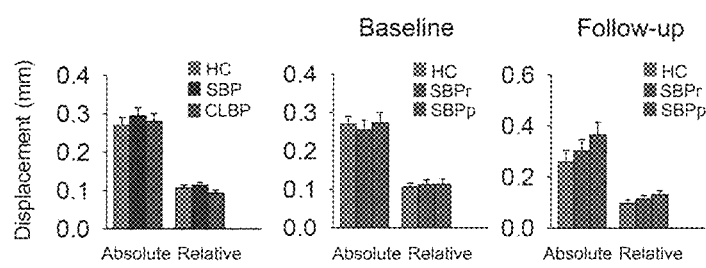
FIG. 16 shows displacement parameters obtained from head motion correction during the resting scans did not differ (ANOVA, p<0.05) between HC, SBP, CLBP (left plot) patients or between HC, SBPr and SBPp patients (mid and right plots) at any point during the study.
Figure 17:
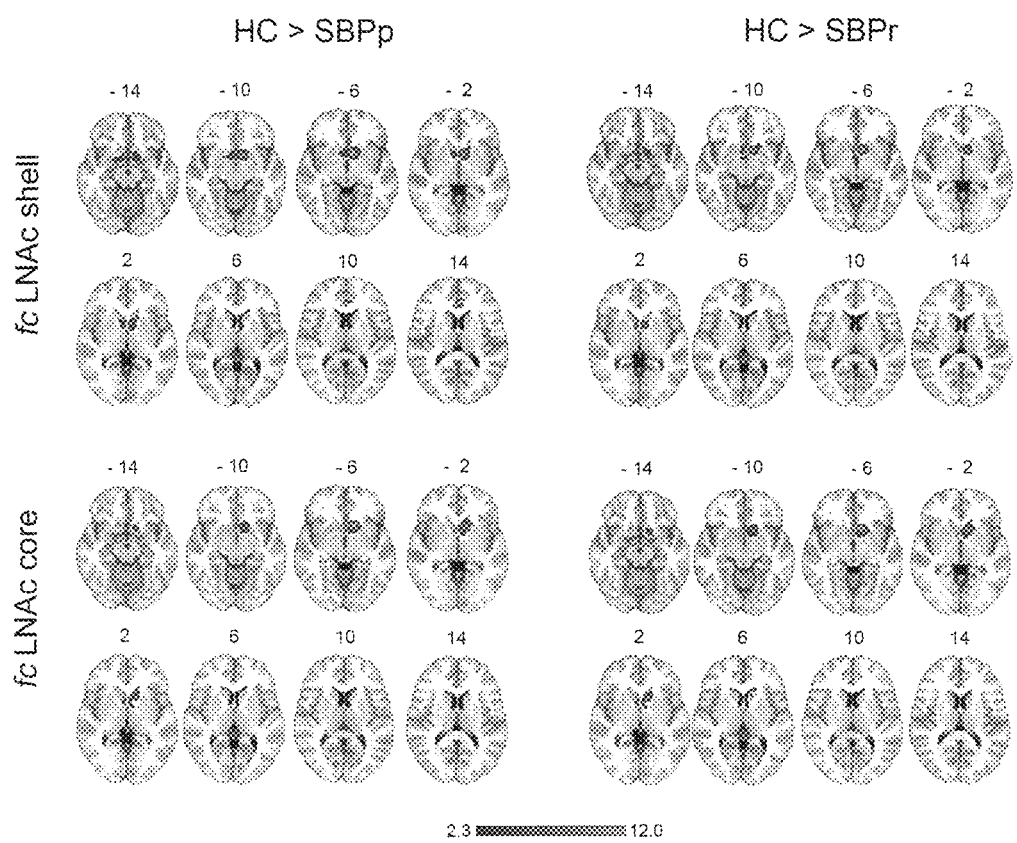
FIG. 17 is a chart in which SBP patients show alteration in functional connectivity of NAc putative shell and core at baseline irrespective of risk of chronicity. Results are unpaired t-test between healthy controls and SBP patients (whole brain corrected, p<0.05).
Figure 18:
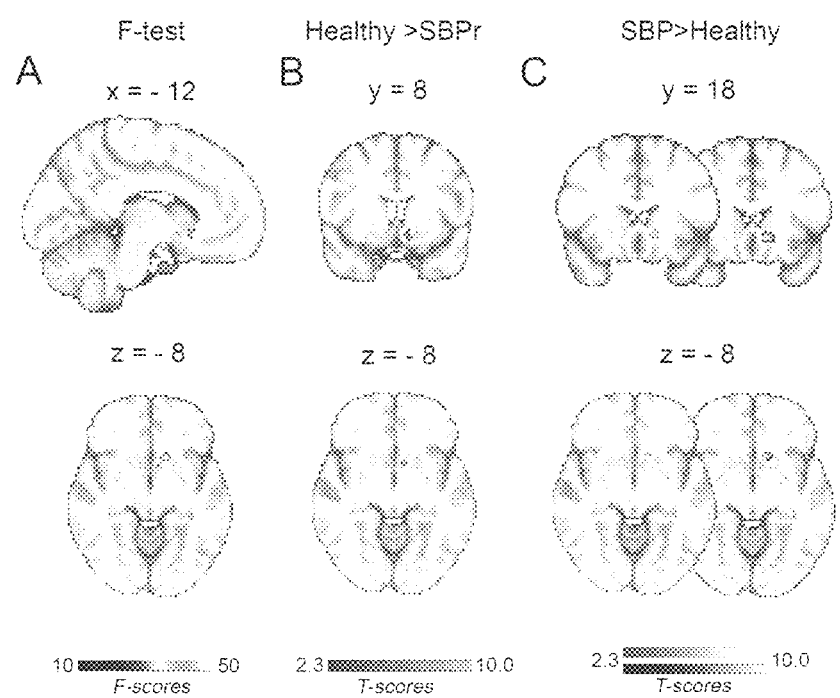
FIG. 18 show effects of time (baseline vs. follow-up, repeated measures analysis) on δ-fc-NAc within the LNAc. SBP patients show a significant change in local NAc connectivity as they transition from sub-acute to chronic pain or recovery (within subject analysis). (A) Differences in functional connectivity (δ-fc-NAc) across all groups (SBPr, SBPp, and healthy controls) (F-test) involving local NAc sub-circuitries shows a significant change over time (p<0.05, corrected). (B) The increased δ-fc-NAc in the HC compared to SBPr at baseline is significantly larger at baseline compared to follow-up (baseline >follow-up) and falls within putative NAc shell. The δ-fc-NAc difference in time between SBPp patients and HC did not reach significance (p=0.16 within the putative NAc shell). (C) The increased δ-fc-NAc in the SBP patients compared to HC at baseline is significantly larger at baseline compared to follow-up and falls within putative NAc core. The difference between SBPp and SBPr observed at follow-up (FIG. 2D) did not show a significant change from baseline to follow-up. All results are whole brain corrected.
Figure 19:
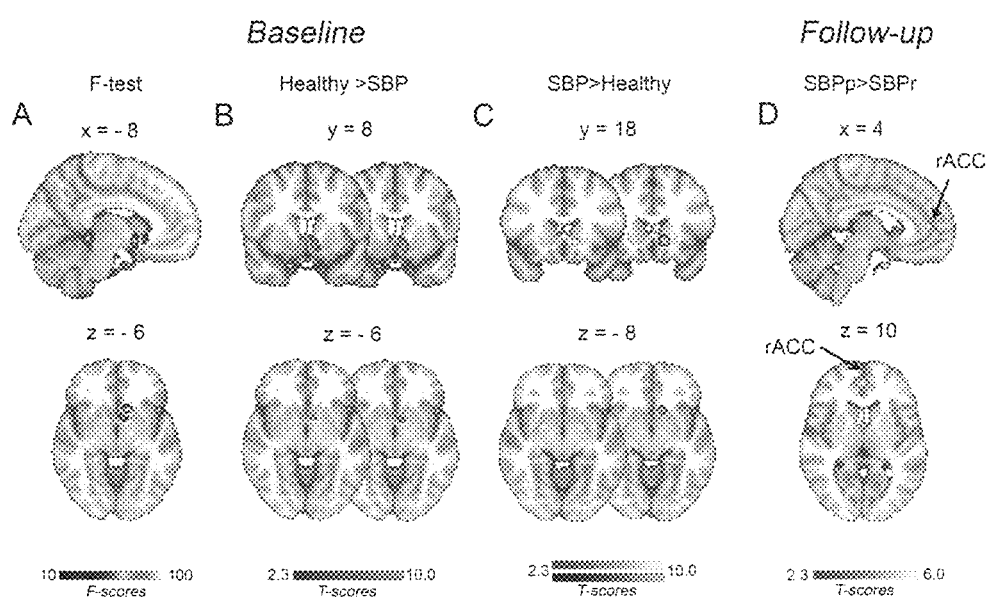
FIG. 19 shows altered left δ-fc-NAc when recovery from back-pain is defined by a 20% drop in pain intensity at follow-up. GLM results for the difference in functional connectivity between LNAc putative shell and core at baseline (A-C) and at follow-up (D). (A) Differences in functional connectivity across all groups (SBPr, SBPp, and healthy controls) (F-test) involves local NAc sub-circuitries. (B) Healthy controls show increased difference in functional connectivity (δ-fc-NAc) between putative shell and core at baseline in the putative shell compared to both SBPp (slices to the left) and SBPr (slices to the right) patients. (C) SBP patients show increased difference in functional connectivity between putative shell and core at baseline in the putative core (T-test). The contrast between SBPp patients and healthy controls is shown in red to yellow; the contrast between SBPr patients and healthy controls is shown in blue to light blue. (D) SBPp patients show increased difference in functional connectivity between putative shell and core within the rostral anterior cinugulate cortex (rACC) at follow-up.

Next it was asked whether the significant change in the volume of NAc in low-back pain patients is accompanied by functional connectivity (fc) changes. Given the well-known structural and functional differences between the nucleus accumbens shell and core demonstrated in animal studies and the recent evidence for the specific role of the NAc shell in acute and chronic pain animal models the functional connectivity of the left and right NAc were studied separately for putative shell and core based on recent parcellations reported using human fMRI (FIG. 2 inset). FIG. 15 shows the average seed fc of the putative NAc shell and core for CLBP patients and healthy controls. CLBP (n=27) patients and healthy controls (n=30) were compared using ANCOVA corrected for age and gender. No significant differences were identified. Head motion parameters estimated using absolute displacement, or relative displacement, were not different between CLBP patients and healthy controls (FIG. 16). Next it was asked whether cortico-striatal connectivity was different in SBPp and SBPr patients compared to healthy controls at baseline (16 SBPp and 19 SBPr patients, and 30 healthy controls) and/or at follow-up (11 SBPp and 14 SBPr patients, and 14 healthy controls) using ANCOVA. At baseline, ANCOVA analysis (i.e. F-test) revealed decreased fc of putative LNAc shell in SBPp and SBPr patients compared to healthy controls within the limbic system. As such, SBPp patients showed decreased fc of putative LNAc shell to left thalamus, right and left NAc, right caudate and rostral anterior cingulate cortex (rACC) (FIG. 17) ($p<0.05$, whole brain corrected). SBPr patients showed decreased fc of putative LNAc shell to left and right NAc and posterior ventral striatum (*pallidum*), right thalamus, and hypothalamus (FIG. 17). No significant difference in fc was observed at follow-up between the 3 groups. Head motion parameters were not different between healthy controls, SBPp and SBPr at baseline or at follow-up (FIG. 16).

Given the different functions of the NAc shell and core next it was asked whether the differences in the fc of the two NAc sub-circuitries are different among the groups. In a first step, the difference in fc between putative shell and core was calculated within each subject using Steiger's approach for "correlated correlations". Hence, for a voxel X putative shell and X (r_sx) and putative core and X (r_cx) correlations were calculated. Next, Steiger's Z-value of the difference between r_sx and r_cx, which was designated as δ-fc-NAc, was derived. The resulting difference Z-maps were finally entered into an ANCOVA analysis using non-parametric permutations. Using this approach, no significant difference between CLBP patients and healthy controls was observed. It was however reasoned that dynamic changes in NAc shell and core connectivity could be occurring in SBP patients at baseline and as they transition to recovery or chronic pain. Therefore, SBPp, SBPr and healthy controls were compared at both visits. At baseline, SBPp, SBPr and healthy controls differed (F-test, $p<0.05$ corrected) in the LNAc (FIG. 2A), and post-hoc analysis showed altered local NAc connectivity in SBP patients compared to controls. Healthy controls showed increased δ-fc-NAc in a cluster falling within the putative NAc shell compared to SBPr and to SBPp patients; SBP patients, on the other hand, showed an increased δ-fc-NAc in a cluster falling within the putative NAc core irrespective of long term risk of transition to chronic pain (FIG. 2B-C). At follow-up, ANCOVA analysis was close to significance (p=0.17) within the rACC and post-hoc analysis showed increased left δ-fc-NAc in the rACC in the SBPp patients compared to SBPr ($p<0.05$, whole brain corrected) (FIG. 2D). The connectivity difference within the rACC was directly correlated to low-back intensity at follow-up across SBPp and SBPr patients (r=0.58, $p<0.01$) (FIG. 2D, scatterplot). Next, to investigate whether these group differences observed at each time point are significantly changing in time it was tested for effects of time using a within subjects (11 SBPp and 14 SBPr patients, and 14 healthy controls) repeated measures design corrected of age and gender. In a first step, the left δ-fc-NAc maps within each subject were registered to a subject specific template derived from the two anatomical images obtained at each timepoint and the template was in turn registered to MNI-space. The within subject difference in time was tested against 10,000 permutations in a second step after accounting for age and gender. As such, the increased left δ-fc-NAc within the putative NAc core and the decreased left δ-fc-NAc within the putative shell in SBP patients compared to healthy controls observed at baseline (FIG. 2A-C) is significantly changing (decreasing) in time (baseline>follow-up within subject analysis, $p<0.05$ corrected; (FIG. 18A-C). The change in time for HC compared to SBPp patients did not reach significance (p=0.16). However, the effects of time on the left δ-fc-NAc within the rACC observed at follow-up between SBPp and SBPr patients (FIG. 2D) is not significantly increased at follow-up compared to baseline. Here it was also tested whether the connectivity results presented in FIG. 2 were affected by the definition of recovery. Therefore, the analysis was repeated based on the 20% criterion for recovery. FIG. 19A shows that, as expected, at baseline, the altered left δ-fc-NAc in SBP patients is independent of risk status. In addition, the increased left δ-fc-NAc connectivity in the rACC at follow-up in SBPp compared to SBPr patients remains significant. Here was also identified resting state data available online from the follow-up visit only in 10 SBPr, 20 SBPp patients and 19 HC and was tested whether the altered left δ-fc-NAc that was observe at follow-up can be identified across sites. However, comparison between the 3 groups using ANCOVA did not yield any significant differences when testing left or right hemispheres.

Spectral Analysis

Figure 20:
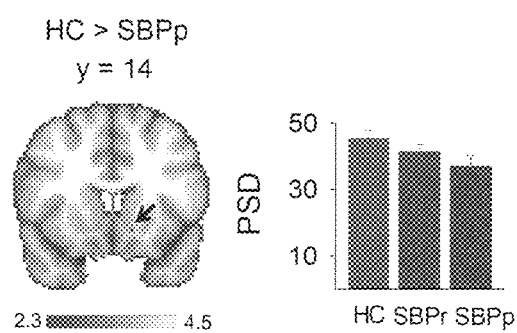
FIG. 20 is a chart with SBPp patients showing loss of power spectral density at follow-up if recovery from back pain is defined as a 20% decrease in pain intensity at follow-up. Brain slice showing loss of PSD of the slow-5 frequency band within the left NAc (p<0.05, ROI corrected) in SBPp patients compared to HC. As depicted in the bar plot on the right, the SBPr patients' PSD fall now between HC and SBPp patients (compare to FIG. 3D).
Figure 21:
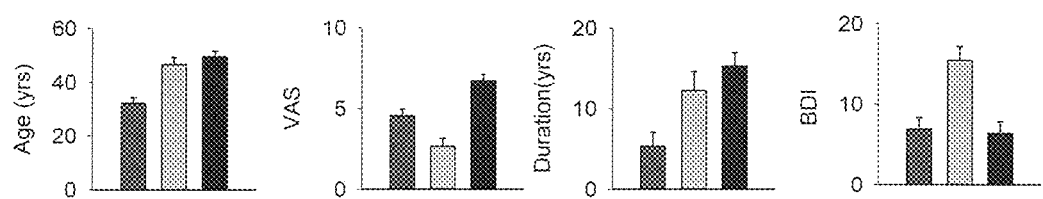
FIG. 21 shows comparison of the CLBP patients originating from the three different sites. The three cohorts differed significantly (one-way ANOVA) on age, back pain intensity and duration, and depression scores (Beck's Depression Index).

The results of the connectivity analysis uncovered differential changes in NAc putative shell and core fc between SBPp, SBPr patients and healthy controls but did not identify a common brain biomarker between SBPp and CLBP patients that represents the "state" of being in chronic back pain. Functional connectivity results suggest that, as pain becomes chronic (i.e. >one year), the NAc sub-circuitries fc show dynamic changes. The power spectral density (PSD) was therefore studied because this approach uncovered meaningful differences among clinical populations including chronic pain patients. PSD of a signal gives an analysis of the distribution of power over the entire frequency range. PSD was calculated for different frequency bands defined in previous neurophysiological and fMRI studies in bilateral NAc and compared among groups using a hypothesis-based approach. It was desired to examine whether altered brain activity oscillations at specific frequency bands may characterize the chronic pain phase. First, PSD was compared between CLBP patients and healthy controls using an unpaired t-test and a bilateral NAc mask. Comparison of PSD within the slow-5 frequency band (0.01-0.027 Hz) only showed significant differences between patients and control (FIG. 3A). CLBP patients showed decreased power for low frequency oscillations in a cluster falling within bilateral putative NAc core and shell ($p<0.05$, ROI corrected). Next, compared were SBPp and SBPr patients and healthy controls at entry into the study and at follow-up using ANCOVA confined to bilateral NAc. This analysis revealed loss of power in the LNAc within the slow-5 frequency band in SBPp patients compared to SBPr patients at follow-up when pain became chronic ($p<0.05$, ROI corrected) (FIG. 3D). The cluster obtained falls within the putative NAc shell. In addition, PSD for the slow-5 band was inversely correlated to reported low back pain intensity across both SBPp and SBPr patients ($r=-0.56$, $p<0.01$) (FIG. 3D). Also tested was whether using a 20% back-pain decrease as a recovery criterion would affect the difference in slow-5 PSD within NAc between groups at follow-up. Using a similar analysis, it was found that SBPp patients show a significant loss in slow-5 PSD compared to healthy controls within the left NAc but are no longer significantly different from SBPr patients ($p=0.21$) (FIG. 20). Since both PSD of the slow-5 frequency band and the difference between putative shell and core fc to rACC were significantly correlated to back pain intensity at follow-up it was asked whether PSD and δ-fc-NAc relate independently to pain intensity. Partial correlations analysis of back pain intensity with both variables (i.e. after removing the variance explained by the other) was significant for both PSD of slow-5 frequency band ($r=-0.43$, $p<0.05$) and fc difference between putative shell and core within rACC ($r=0.46$, $p<0.05$). Next it was asked whether this loss of power in slow-5 frequency band is reproducible in CLBP patients studied at different sites and made accessible through www.openpain.org. Applying an identical analytic approach and pooling data collected in FIG. 3E, it was also observed loss of PSD within the slow-5 frequency band in RNAc in CLBP patients compared to healthy controls ($p<0.05$, ROI corrected), despite the significant demographic and clinical heterogeneity of the CLBP patients' samples analyzed (FIG. 21). If the loss of PSD within the slow-5 frequency band was directly related to the loss of volume in the NAc, loss of PSD within other the frequency bands (i.e. slow-2, 3 and 4) would have also been observed. In addition, the loss of PSD within the slow-5 frequency band would have been apparent within the SBPp patients at baseline because these subjects do show a significantly smaller NAc at entry into the study. Nevertheless, a multiple regression was run using the CLBP patients and healthy controls PSD data within bilateral NAc as a dependent variable and age, sex, group (CLBP vs. HC) and NAc volume as independent variables. Group remains a significant predictor of slow-5 PSD (mean PSD±SEM for HC=47.0±1.6 and for CLBP patients=39.8±1.6; $\beta=3.63$; $F_{(1,46)}=9.0$, $p=0.0043$). The NAc volume did not significantly predict PSD ($\beta=0.0082$; $p=0.15$). Similar multiple regression was run on the SBPp, SBPr and HC PSD data at follow-up. Group remains a significant predictor of slow-5 PSD ($\beta=5.81$; $F(2,34)=6.4$; $p=0.0042$), whereas LNAc volume is not ($p=0.81$).

NAc volume and slow-5 PSD can accurately classify chronic low back pain patients The volumetric and PSD results suggest that these features are potential predictors of being in chronic pain. Given that the slow-5 PSD in the nucleus accumbens showed the most robust reproducibility across studies and sites we first tested the discriminative power of slow-5 PSD within the left and right NAc separately in classifying new data from the Chicago longitudinal study available from their follow-up visit (visit 4), using a simple cut-off for evaluation of the areas under the ROC curve. Slow-5 PSD extracted from the LNAc accurately classified 10 SBPr and 20 SBPp patients with an AUC=0.75 ($p<0.05$) (FIG. 4A), and 14 CLBP patients and 19 HC with an AUC=0.73 ($p<0.05$) (FIG. 4B). The PSD values in CLBP and HC were corrected for age (FIG. 27). Next, it was desired to add the volume of the nucleus accumbens as a feature in a linear model to classify chronic back pain patients. Therefore, a linear SVM model was trained on data pooled from this study and other data (45 CLBP patients and 65 HC subjects) using NAc slow-5 PSD and volume for each hemisphere separately. Next, using the model weights, the 10 SBPr vs. 20 SBPp patients were classified. Features extracted from the LNAc accurately classified SBPr and SBPp patients with AUC=0.72 ($p<0.05$). (FIG. 4C). The model was also tested on the 14 CLBP patients and 19 HC subjects available from the same follow-up visit part of the Chicago longitudinal data. The prediction in this case did not reach significance (AUC=0.61, $p=0.15$). The results presented in FIGS. 4A-B and C-D respectively use the same test data set hence the test data set was used twice in the analysis.

DISCUSSION

Patients suffering from low-back pain showed smaller NAc volume that predated the transition to the chronic phase and showed loss of PSD within the slow-5 (0.01-0.027 Hz) frequency band that developed as pain became chronic. The loss of PSD is a robust and novel finding that was reproduced across samples and across sites, and accurately classified chronic low-back pain patients from an independent data set. In addition, NAc sub-circuitries exhibited dynamic changes in functional connectivity as low-back pain patients transitioned from the sub-acute to the chronic phase. Altered local NAc differential connectivity between putative NAc shell and core was associated with the sub-acute phase irrespective of risk of "chronification" whereas increased differential connectivity between putative shell and core to the rACC was associated with the chronic phase and co-varied directly with reported back pain intensity. Time effects analysis confirmed the early involvement of the NAc sub-circuitry during the sub-acute phase; however, the increased differential connectivity of the left NAc to the rACC did not significantly change in time and hence remains to be confirmed in future studies. In addition to the NAc, the amygdala volume at baseline was smaller in SBPp compared to SBPr patients and accurately classified patients by long-term risk for CLBP. The findings agree with preclinical data showing a critical role for the NAc shell in the transition to chronic pain and the role of the NAc and its connections to the prefrontal cortex in modulating peripheral nociceptive input. They are also consistent with recent reports demonstrating that amygdala and hippocampus volume and NAc connectivity to the medial prefrontal cortex can predict the risk of transition to chronic pain.

Chronic pain patients suffer from anhedonia and decreased motivation. CLBP patients in particular exhibit impaired value-based decision-making, and disrupted hedonic perception and satiety signals of highly palatable food. Studies of animal models of chronic pain have replicated some of these findings and linked reduced motivation to a hypodopaminergic tone in both patients and animal models. The NAc is well known to play a central role in hedonic and motivated behavior. It contains an abundance of ti-opioid receptors, receives meso-limbic dopaminergic projections and is thought to act as a limbic-motor interface translating motivation into motor action. Mid-brain dopaminergic projections to the NAc fire in response to both rewarding and aversive stimuli. Brain areas where hedonic and/or incentive value of stimuli are encoded such as orbito-frontal and ventro-medial prefrontal cortex and anterior insula send projections to the NAc which in turn projects to the ventral *pallidum* and lateral hypothalamus. This anatomy allows the NAc to access value signals (e.g. hunger, pain) and to send efferent output to the extra-pyramidal motor system, hence controlling action selection between competing appetitive drives. Manipulation of the $\mu$-opioid receptor within the NAc alters hedonic reactions to appetitive stimuli and choices of appetitive rewards. Alterations in NAc structure, activity and connectivity in back pain patients are therefore consistent with the observations of disrupted hedonic and motivated behavior in chronic pain. Some NAc alterations (e.g. smaller volume) predate the development of CLBP suggesting that chronic pain and disruption in motivation and hedonic encoding might share common neural vulnerabilities. Importantly, these structural and functional alterations in the NAc circuitries are independent of depression and anxiety ratings. In fact, major depression is associated with an enlargement of nucleus accumbens volume, which shrinks after successful treatment. The opposite findings could henceforth help us untangle the overlapping pathophysiology of chronic pain and major depression.

NAc shell and core play different roles in value-based associative learning. The core is thought to mediate cue-outcome association (i.e. similar to the dorsal striatum) and the shell is thought to encode hedonic (positive or negative) value of stimuli. While altered NAc structure and connectivity implies generalized changes in motivated behaviors in back pain patients, altered NAc connectivity specifically putative shell in at risk back-pain (i.e. SBPp) could be associated with disrupted hedonic encoding observed in chronic pain. Putative shell develops also loss of PSD within the slow-5 frequency band in SBPp patients at follow-up whereas both putative shell and core exhibit this change in the CLBP patients. These observations suggest that the NAc shell activity is affected early during pain "chronification" and are consistent with recent animal studies showing that NAc shell is sufficient to drive peripheral nociception and pain induced negative affect. The altered $\delta$-fc-NAc in SBP patients at baseline, on the one hand, and the increased $\delta$-fc-NAc to rACC connectivity in SBPp patients at follow-up on the other hand suggests that NAc connectivity is locally altered during sub-acute pain processing and spreads to other limbic regions as pain becomes chronic.

The sub-acute back pain patients were recruited if their pain intensity was larger than 20/100 on a VAS scale and the observed average back-pain rating was around 30/100 at baseline. This is relatively low level of pain compared to clinical pain studies in the literature. Nevertheless, back pain intensity fluctuates on a rather short time scale (minutes) and the patients reported constant back pain more days than not. While patients suffering from a milder form of low-back pain were included, the sample of SBP patients had a broad range of pain intensity levels (FIG. 2D). In addition, SBPr and SBPp patients had similar levels of pain at baseline.

In conclusion, the NAc functional and structural characteristic are central to the pathophysiology of chronic low back pain. Loss of PSD within the slow-5 frequency band of NAc activity in particular is a signature of chronic pain that showed significant accuracy in classifying chronic low back pain patients, and is consistent with the new neuroimaging and pre-clinical literature on the role of NAc persistence of clinical pain. The measurement of this feature follows standard brain image analysis procedures and is generalizable across scanners and laboratories.

Materials and Methods

Participants

Data Collected

The study recruited 40 SBP patients (16 females, average age±standard error of the mean (SEM)=31.7±1.7 years), 28 CLBP patients (17 females, 32.2±2.0 years), and 30 healthy controls (HC) (14 females, 31.1±2.0 years). Chronic low back pain (CLBP) patients were studied at one time point only. The SBP patients and HC were followed-up longitudinally for a median duration of approximately one year. All SBP patients reported low back pain of at least 20/100 on visual analogue scale (VAS, 0-100, where 100=maximum imaginable pain and 0=no pain) for the previous 6 to 16 weeks with no back pain or pain at other locations in the 12 months prior to the onset of the current episode. CLBP patients reported low back pain of at least 30/100 on a VAS for at least one year. Participants were excluded if they reported pain at other locations, systemic illnesses, psychiatric diseases, prior traumatic brain injury, or if they tested positive for a controlled substance on a urine toxicology test. All patients reported no or less than mild depression (reported Beck's Depression Inventory (BDI) score between 14 and 19) except three CLBP patients who reported moderate depression (BDI<28) Table 22, 24 for complete demographic and clinical data). Data collection took place between July 2014 and April 2019.

Longitudinal Follow-Up

Of the forty SBP patients, thirty-five (87.5%) presented for follow-up (32.5±1.9 years, 14 females) and completed questionnaires, twenty-six (65%) consented to scan, five were lost to follow-up. Of the thirty healthy controls, 16 (53.3%) presented for follow-up (age=31.6±2.5 years, 7 females) fourteen (46.7%) consented to scan, eleven (36.7) were not yet due for follow-up, and five (16.7%) were lost to follow-up. The median duration at follow-up was 59.4 weeks (FIG. 24). Consistent with the recommendations of the Initiative on Methods, Measurements and Pain Assessments in Clinical Trials (IMMPACT) SBP patients were dichotomized into recovered back pain patients (SBPr, n=19) if their back-pain intensity dropped 30% on the VAS relative to the pain at entry into the study or into persistent back pain patients (SBPp, n=16) otherwise. SBP patients who dropped out at follow-up and SBP patients who completed the follow-up visit did not differ on rated back pain intensity at entry into the study (dropped out=3.4±1.0, completed=3.1±0.3, p=0.72 on the VAS), or pain duration in weeks (dropped out=8.5±3.6, completed=9.5±0.7 weeks; p=0.64). All participants gave informed consent for inclusion in the study.

Data Made Available Online

To validate the findings in an independent dataset, data sets collected at different sites were obtained. Data were obtained from the OpenPain Project (OPP) database (https://www.openpain.org). Therefore, three additional resting-state fMRI data sets were analyzed. The first data set was collected and included 24 CBP patients (11 females, 49.5±2.0 years) and 30 healthy controls (13 females, 48.5±1.7 years). The second data set was also collected as part of a longitudinal study using fMRI to study the transition from sub-acute to CLBP. This data included participants studied during the follow-up visit: 14 CLBP patients (6 females, 46.9±1.9 years), 19 healthy controls (8 females, 37.5±1.6 years), and 30 SBP patients (15 females, 45.6±1.8 years). The third data set was collected and included 20 CBP patients (12 females, 46.7±2.6 years) and 38 healthy controls (14 females, 38.9±2.2 years). Both data sets are freely available at www.openpain.org.

Pain Characteristics, Mood and Affect

Patients reported their pain using the short form of the McGill Pain Questionnaire (sfMPQ), the Neuropathic Pain Scale, and the Pain Catastrophizing Scale at all visits. They reported their mood and anxiety levels using the Beck's Depression and the Beck's Anxiety Indices.

Scanning Parameters

Participants underwent an anatomical T1-weighted scan, and two-consecutive 6-minutes long resting state scans. Siemens 3.0 T Trio B magnet equipped with a 32 channels head-coil was used to acquire the images. MPRAGE 3D T1-weighted acquisition sequence was as follows: TR/TE=1900/2.52 ms, flip angle, 9°, matrix 256×256 with 176-1 mm slices acquired in the same orientation as the functional data. During the functional scans participants were asked to stare at a cross hair; the functional acquisition sequence was as follows: TR/TE=1000/30.0 ms, flip angle, 60°, matrix 110×110×60 with 2×2×2 mm voxels, and an acceleration factor of 4.

Volume Calculations

Structural data were analyzed with the standard automated processing stream of the Functional Magnetic Resonance Imaging of the Brain (FMRIB) software library (FSL) 5.0.10 that shows high reliability across laboratories. The analysis sequence includes skull extraction, a two-stage linear subcortical registration, and segmentation using Integrated Registration and Segmentation Tool (FIRST) part of FMRIB. The volumes of right and left nucleus accumbens (NAc), amygdala, hippocampus and thalamus were calculated for each participant and normalized to standard Montreal Neurologic Institute (MNI) space. The normalization coefficient was calculated using FSL SIENA. Quality control included: (i) visual inspection of subcortical segmentation to identify gross mismatches between underlying anatomy and FIRST output; (ii) identification and exclusion of outliers defined using Tukey's method; and (iii) comparison of signal to noise ratio (SNR) within each subcortical structure across groups. SNR was calculated as the mean signal within a certain structure minus the mean signal outside the brain divided by the standard deviation of the signal outside the brain. Outliers were defined independently for each structure. Three participants' data was excluded as such. Importantly, removing these individuals did not change the statistical results.

Subcortical volume calculations were repeated using the standard automated cortical and subcortical segmentations by Freesurfer 5.0 (http://surfer.nmr.mgh.harvard.edu/) to check volume reproducibility of the results across different segmentation algorithms. Freesurfer's analysis sequence includes motion correction, removal of the skull using watershed/surface deformation procedure, normalization in Talairach space, and segmentation of the brain structures based on the existing atlas containing probabilistic information on the location of the structures.

Functional MRI Preprocessing

Two six-minutes long resting state scans were acquired consecutively while participants stared at a cross hair. The preprocessing of each participant's fMRI time series was performed using FMRIB Expert Analysis Tool (FEAT). The sequence was published previously by the group and included skull extraction using Brain Extraction Tool, head motion correction, band pass filtering (0.008-0.2 Hz), and spatial smoothing (5-mm full width at half maximum Gaussian blur). Several sources of spurious variance were removed from the data with linear regression. The six parameters obtained by rigid head motion correction along and their temporal derivative, and 10 components derived from noise regions of interest (ROIs) were regressed out from the data. The latter components were identified following an anatomical approach as described in. Briefly, cerebro-spinal fluid and white matter timeseries were extracted from each subject's fMRI data based on masks derived from the high-resolution anatomical image using FSL FAST. Next, principal component analysis was applied to obtain the first 5 white matter and first 5 CSF components. After preprocessing functional scans were registered into the MNI space. Registration to high resolution structural and/or MNI images was carried out using FLIRT. Registration from high resolution structural to MNI space was then further refined using FNIRT nonlinear registration.

Seed Based Analysis

Seed based connectivity was determined following a well-defined method and used previously by the group. To investigate whether brain networks correlated with specific regional activity (seed) as a function of group, seeds were defined from a probabilistic parcellation of putative nucleus accumbens shell and core (see results section). Average BOLD time course of all voxels within the ROIs were extracted and then the correlation coefficient between this time course and the time variability of all brain voxels were computed using Matlab. Head motion can cause spurious but spatially structured changes in functional correlations. To minimize these effects, all subjects were movement-scrubbed. This procedure uses temporal masks to remove motion-contaminated data from regression and correlation calculations by excising unwanted data. Frames in which collective displacement across all 6 rigid body movement correction parameters exceeded FD>0.5 mm (assuming 50 mm cortical sphere radius) were identified. Frames flagged by this criterion were excluded. Runs with >40% frames flagged were omitted from analyses. Correlation coefficients were converted to a normal distribution using the Fisher z-transform. These values were then converted to z-scores (i.e. normalized correlation values) by dividing by the square root of the variance, estimated as $1/\sqrt{df-3}$, where df represents the degrees of freedom in the measurements (i.e. the number of volumes acquired). Because the BOLD time courses of consecutive samples are not statistically independent, the degrees of freedom were corrected by a factor according to Bartlet theory. Group differences in seed based connectivity were identified using permutation based inference to allow rigorous comparisons of significance within the framework of the general linear model with $p<0.05$. Group differences were tested against 10,000 random permutations, which inherently accounts for multiple comparisons, using Randomise part of FSL. Group contrast clusters were identified using threshold-free cluster enhancement (TFCE) method, which bypasses the arbitrary threshold necessary in methods that use voxel-based thresholds. To test for the effects of time (baseline vs. follow-up) on functional connectivity a repeated measure (baseline vs. follow-up) was used by groups (HC vs. SBPp vs.SBPr) ANCOVA. First a subject specific template for each participant using their baseline and follow-up anatomical scans to account for possible longitudinal changes in anatomy was generated. The template was generated using Free-Surfer's command "mri_robust_template". Next functional connectivity maps from baseline and follow-up were registered to this template which in turn was registered to the MNI space. Finally, the within subject GLM analysis was run to test for time effects using 10,000 permutations (randomize, FSL).

Spectral Analysis

Spectral analysis was performed using custom Matlab (The MathWorks, 2010) routines and is similar to methods reported previously. Frequency power of the BOLD signal was determined voxel wise using Welch's method and normalized by dividing by total power. This normalization was necessary as the absolute power of BOLD remains unknown simply because the absolute intensity of BOLD signal in time space is also unknown and assigned an arbitrary value in all standard fMRI analyses. The average power of each frequency band slow-5 (0.01-0.027 Hz), slow-4 (0.027-0.073 Hz), slow-3 (0.073-0.198 Hz) and slow-2 (0.198-0.5 Hz) was calculated at each voxel and converted into four different maps for each subject. Individual subject maps were transformed into standard space as described in the preprocessing section and multiplied by a standard gray matter mask. Subject-level maps were transformed to z-score maps by subtracting the mean voxel wise power for the entire brain and dividing by the standard deviation. Group differences were generated using a similar non-parametric permutation and thresholding approaches described under seed-based analysis.

Support Vector Machine Learning and Model Building

Using the slow-5 power spectral density and nucleus accumbens volume of each hemisphere separately as features in a support vector machine (SVM) learning analysis to classify subjects: SBPp vs. SBPr patients or CLBP patients vs. HC. The SVM model was trained and tested on independent datasets collected at different institutions. Features were selected and their weights were learned without using information from the test set. For validation, the trained models were used to predict outcomes in the test set. For models combining more than one measure, it was learned the relative weights of each measure using a linear SVM. Free hyperparameters were first chosen from a grid of proposed values using cross-validation within the training set, and then models were fit to the full training data set using the optimal hyperparameters. Finally, models were tested on an independent data set. The model was trained on data collected and on data available online at www.openpain.org. The test datasets (Table S6) were not used in any of the previous analyses or during the training of the SVM model. Data was harmonized from different scanners using the Combat method. Next, a linear SVM was trained to discriminate between HC and CBP subjects in the training datasets pooled together, and evaluated the discriminative power of the distance to the decision hyperplane in two sets of subjects from the Chicago's longitudinal cohort visit 4 (HC vs CLBP, and SBPr vs. SBPp patients) as quantified by the area under the receiver operating characteristic (ROC) curve (AUC). Significance of the result was established by random permutation of the validation set labels ($10^3$ permutations). The LinearSVC implementation in scikit-learn was used with default parameters with the following exceptions: "loss" parameter was set to "hinge", "class_weight" was set to "balanced", and "C" was chosen by internal cross validation (grid search, 5 internal cross validation folds) from 8 possible values ranging between $10^{-5}$ and $10^3$ equally spaced in logarithmic units. The code is freely available at this link: https://github.com/polosecki/cbp_accumbens_ML. In imbalanced test datasets, both classes were given equal weights because the AUC depends only on the fraction of errors in one class, and the fraction of hits in the other class as the decision threshold is changed. The fraction of labels for each class remained fixed during permutation testing, ensuring that significant results could not be explained by the distribution of labels in the test set.

Statistical Analyses

Statistical analyses of demographic and clinical variables and of extracted sub-cortical volumes were performed using Statistica Software (TIBCO, Inc.). Between-group analysis was performed using general linear model or ANOVA. All analyses of sub-cortical volumes accounted for age, sex and intracranial volumes. Linear regression analyses was used to investigate the relationships between reported pain on the VAS and brain measures.

Another Example is Presented Below:

Chronic pain is highly prevalent. To date, the diagnosis of chronic pain relies only on subjective reports provided by the patient. There is no one medical test to diagnosis or confirm that an individual patient has chronic pain or not. The invention described below provides the first available quantitative test to diagnose chronic pain in human subjects.

The Tool

Patients suffering from chronic low back pain (i.e. pain duration >3 months) were studied using functional brain imaging. The technique measures the fluctuations of electrical brain activity, only indirectly though by measuring brain regional blood flow. The signal is called Blood Oxygen Level Dependent (BOLD) signal. BOLD can be measured within a span of minutes. In the case the total time needed for this measurement was 30 minutes. A Tesla 3 MRI magnet was used.

The Findings

Frequency content of brain activity was looked at and broken down to 4 different frequency bands. The transformation of the brain signal from the time domain to the frequency domain uses Fourier Transformation. The 4 different frequency bands that were examined are slow-5 (0.01-0.027 Hz), slow-4 (0.027-0.073 Hz), slow-3 (0.073-0.198 Hz) and slow-2 (0.198-0.5 Hz).

In a first step loss of power spectral density (PSD) (i.e. energy) was identified within the slow-5 frequency band in an area in the brain called the nucleus accumbens in the chronic low back pain patients compared to the healthy controls. The importance of the finding lies in the fact that this was observed across 3 different cohorts of chronic low back pain patients studied at 3 different laboratories on two different continents.

Next, in two additional cohorts originating from New Haven and Chicago it was accurately classified (i.e. to blindly identify them) chronic low back pain patients compared to healthy controls.

Therefore, the loss of low frequency fluctuations in the slow-5 frequency band in the Nucleus Accumbens in the brain can be used as a signature of chronic low back pain and possibly all kinds of chronic pain.

Potential Clinical Use

The loss of PSD within the slow-5 frequency band can be used as the first quantitative medical test to diagnose chronic pain (any chronic pain) using a simple cut-off approach very similar to a pregnancy test (i.e. yes, no test). In addition, it can be used to test any treatment effects like medications for pain or psychotherapy for pain or physical therapy for pain. An important commercial use would be pharmaceutical companies using the measure both in humans and animals to test new drugs for chronic pain. Please note that the measure can be obtained in animal models of chronic pain using the same approach as the one used in the work. Please note also that the agreed upon definition of chronic pain is pain that lasts more than 3 months.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of identifying chronic pain in a patient comprising:
    using functional magnetic resonance imaging (fMRI), performing a brain scan in nucleus accumbens (NAc) of a patient brain including extracting activity from the NAc;
    breaking down frequency bands of the brain scan to extract information in a 0.01-0.027 Hz frequency band;
    using the extracted activity to compare to database information, the database information including fMRI data obtained from healthy subjects; and
    using the compared data to determine if patient is a chronic pain patient.

2. The method of identifying chronic pain in a patient according to claim 1 performing a brain scan in the NAc of a patient includes performing a resting state brain scan.

3. The method of identifying chronic pain in a patient according to claim 1 including after the step of using the compared data to determine if patient is a chronic pain patient, treating the patient and repeating the steps of claim 1 to evaluate the effect of the treatments.

4. The method of identifying chronic pain in a patient according to claim 1 including an initial step of confirming patient experiencing pain of at least 20/100 on a visual analogue scale.

5. The method of identifying chronic pain in a patient according to claim 1 wherein the step of using the extracted activity to compare to database information includes calculating a normalization coefficient.

6. The method of identifying chronic pain in a patient according to claim 1 including an initial step of distribute questionnaire to patient, the questionnaire including pain level and mood and anxiety levels.

7. The method according to claim 2 wherein the resting state brain scan uses Blood Oxygen Level Dependent (BOLD) as a measure.

8. The method of identifying chronic pain in a patient according to claim 1 including after the step of extracting activity from NAc, performing a Fourier transform to obtain frequency content.

9. The method of identifying chronic pain in a patient according to claim 1 including using the extracted activity to compare to database information obtained from scans of a plurality of healthy individuals.

10. The method of identifying chronic pain in a patient according to claim 1 wherein the data information includes measured activity obtained from scans of a plurality of healthy individuals.

11. The method of identifying chronic pain in a patient according to claim 1 wherein the database information includes cutoff measurements for determining if the patient is a chronic pain patient.

12. The method of identifying chronic pain in a patient according to claim 1 wherein the chronic pain is a chronic back pain.

13. A method of identifying chronic pain using low frequency fluctuations in nucleus accumbens comprising:
    performing a resting state scan of a nucleus accumbens using Blood Oxygen Level Dependent (BOLD) as a measure;
    extracting activity from the nucleus accumbens;
    performing a Fourier transform to obtain content within a 0.01-0.027 Hz frequency band;
    using the extracted activity to compare to database information which includes cutoff measurements for determining if a patient is in a state of chronic pain; and
    using the compared data to determine if the patient is in said state of chronic pain.

14. The method of identifying chronic pain in a patient according to claim 13 including:
    treating the patient; and
    repeating the steps of performing a resting state scan of the nucleus accumbens using BOLD as a measure, extracting activity from nucleus accumbens, performing a Fourier transform to obtain content within a 0.01-0.027 Hz frequency band, using the extracted activity to compare to database information and using the compared data to determine if patient is in a state of chronic pain.

15. A method of identifying chronic pain in a patient comprising:
    using fMRI, monitor activity of a plurality of healthy subjects in nucleus accumbens of each subject's brain within a 0.01-0.027 Hz frequency band and enter measured data from the monitored activity into a database;
    determine distribution of the measured data in the healthy subjects to determine cutoff on measure for healthy patient;
    performing a resting state scan of the nucleus accumbens using Blood Oxygen Level Dependent (BOLD) as a measure;
    extracting activity from nucleus accumbens;
    performing a Fourier transform to obtain content within a 0.01-0.027 Hz frequency band;
    using the extracted activity to compare to database information which includes cutoff measurements for determining if a patient is a chronic pain patient; and
    using the compared data to determine if the patient is a chronic pain patient.

16. The method of identifying chronic pain in a patient according to claim 15 wherein extracting activity from the nucleus accumbens includes analysis of the power spectral density of nucleus accumbens resting state activity where there is a loss of power in the 0.01-0.027 Hz frequency band.

17. The method of identifying chronic pain in a patient according to claim 16 including performing a Fourier transform analysis at the 0.01-0.027 Hz frequency band to determine if the patient is in a state of chronic pain.

18. The method of identifying chronic pain in a patient according to claim 15 including:
   after the step of using the compared data to determine if patient is a chronic pain patient, treating the patient and repeating the steps of performing a resting state scan of the nucleus accumbens using BOLD as a measure, extracting activity from nucleus accumbens, performing a Fourier transform to obtain content within a 0.01-0.027 Hz frequency band and using the extracted activity to compare to database information which includes cutoff measurements for determining if the patient is in a state of chronic pain.

* * * * *